(12) United States Patent
Puetz et al.

(10) Patent No.: US 6,890,959 B2
(45) Date of Patent: May 10, 2005

(54) AMINOMETHYL-PHENYL-CYCLOHEXANONE DERIVATIVES

(75) Inventors: Claudia Puetz, Dueren (DE); Helmut Buschmann, Aachen (DE); Babette-Yvonne Koegel, Langerwehe-Hamich (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/189,184

(22) Filed: Jul. 5, 2002

(65) Prior Publication Data

US 2003/0096811 A1 May 22, 2003

Related U.S. Application Data

(63) Continuation of application No. PCT/EP00/13282, filed on Dec. 27, 2000.

(30) Foreign Application Priority Data

Jan. 5, 2000 (DE) .......................................... 100 00 311

(51) Int. Cl.$^7$ ............................................. A61K 31/135
(52) U.S. Cl. ...................... 514/657; 514/656; 514/646; 564/428; 564/305; 564/443; 564/442
(58) Field of Search ................................ 564/305, 428, 564/443, 442; 514/657, 656, 646

(56) References Cited

U.S. PATENT DOCUMENTS

| | | | |
|---|---|---|---|
| 5,708,026 A | | 1/1998 | Crossley et al. |
| 5,733,936 A | | 3/1998 | Buschmann et al. |
| 5,801,201 A | | 9/1998 | Graudums et al. |
| 6,077,845 A | * | 6/2000 | Puetz et al. ................. 514/297 |
| 6,274,768 B1 | * | 8/2001 | Puetz et al. ................. 564/443 |

FOREIGN PATENT DOCUMENTS

| | | |
|---|---|---|
| DE | 19525137 | 1/1997 |
| EP | 0386839 | 9/1990 |
| EP | 0780369 | 1/2000 |
| WO | 95/21813 | 8/1995 |
| WO | 99/64411 | 12/1999 |

OTHER PUBLICATIONS

E. Borrione, et al., "Synthesis and cycloaddition reactions of ethyl glyoxylate imines. Synthesis of Substituted Furo–[3,2–c] quinolines and 7H–Indeno[2,1–c] quinolines" Journal of Heterocyclic Chemistry, vol. 25, No. 1831, pp. 1831–1835, 1988.

E. Borrione, et al., "Diastereofacial Selectivity in the Cycloaddition of Chiral Glyoxylate Imines to Cyclopentadiene and Indene: Synthesis of Optically Active Tetrahydroquinolines" Journal of the Chemistry Society, vol. 12, No. 9, pp. 2245–2250, 1989.

R. W. Carling, et al., "2–Carboxytetrahydroquinolines. Conformational and Stereochemical requirements for antagonism of the glycine site on the N–methyl–D–aspartate receptor" Journal of Medicinal Chemistry, vol. 35, No. 11, pp. 1942–1953, 1992.

International Search Report.

* cited by examiner

*Primary Examiner*—Samuel Barts
(74) *Attorney, Agent, or Firm*—Crowell & Moring LLP

(57) ABSTRACT

Aminomethyl-phenyl-cyclohexanone derivatives of formula I or Ia,

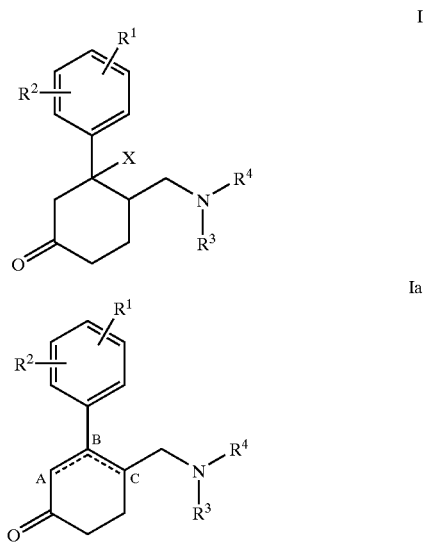

their diastereomers, enantiomers and salts formed with a physiologically tolerated acid. Also disclosed are processes for preparing the same, pharmaceutical compositions comprising the same, and methods of using the same for the treatment of pain, inflammatory reaction, allergic reactions, depression, drug abuse, alcohol abuse, gastritis, cardiovascular disease, respiratory tract disease, coughing, mental illness, epilepsy, urinary incontinence, itching, and diarrhoea.

89 Claims, No Drawings

AMINOMETHYL-PHENYL-CYCLOHEXANONE DERIVATIVES

CROSS REFERENCE TO RELATED APPLICATIONS

The present application is a continuation of international patent application no. PCT/EP00/13282, filed Dec. 27, 2000, designating the United States of America, the entire disclosure of which is incorporated herein by reference. Priority is claimed based on Federal Republic of Germany patent application no. 100 00 311.7, filed Jan. 5, 2000.

BACKGROUND OF THE INVENTION

The present invention relates to aminomethyl-phenyl-cyclohexanone derivatives and processes for their preparation, the use of aminomethyl-phenyl-cyclohexanone derivatives for the preparation of medicaments and medicaments comprising aminomethyl-phenyl-cyclohexanone derivatives.

Treatment of chronic and non-chronic states of pain is of great importance in medicine. There is a worldwide need for pain treatments with a good action for target-orientated treatment of chronic and non-chronic states of pain appropriate for the patient, by which is to be understood successful and satisfactory pain treatment for the patient. This manifests itself in the large number of scientific works which have been published in the field of applied analgesia and basic research in nociception in recent years.

Conventional opioids, such as morphine, have a good action in the treatment of severe to very severe pain. However, their use is limited by their known side effects, e.g. respiratory depression, vomiting, sedation, constipation, addiction, dependency and development of tolerance. They can therefore be administered over a relatively long period of time or in relatively high dosages only if particular safety precautions are taken, such as specific prescription instructions (Goodman, Gilman, The Pharmacological Basis of Therapeutics, Pergamon Press, New York 1990). They furthermore show a lower activity with some states of pain, in particular neuropathic pain.

Tramadol hydrochloride—(1RS,2RS)-2-[(dimethylamino)methyl]-1-(3-methoxyphenyl) cyclohexanol hydrochloride—is another known therapeutic for treatment of severe pain. It occupies a special position among analgesics having an action on the central nervous system, inasmuch as this active compound brings about potent inhibition of pain without the side effects known of opioids (J. Pharmacol. Exptl. Ther. 267, 331 (1993)), both the enantiomers of tramadol and the enantiomers of tramadol metabolites participating in the analgesic action (J. Pharmacol. Exp. Ther. 260, 275 (1992)). Needless to say, tramadol is also not without its own side effects.

Substituted aminomethyl-phenyl-cyclohexanone derivatives are already described in DE 195 25 137 A1 (Grünenthal GmbH), as well as in German Patent Application 198 30 105.7-44 (Grünenthal GmbH). However, these are always synthesis precursors which are not described themselves as active compounds in medicaments or as having an analgesic action.

An object on which the invention was based was to provide substances which have an analgesic action and are suitable for treatment of pain. These substances should furthermore have as few side effects as possible, such as nausea, vomiting, dependency, respiratory depression or constipation.

DESCRIPTION OF THE INVENTION

This object is achieved by the aminomethyl-phenyl-cyclohexanone derivatives according to the invention. The invention therefore provides aminomethyl-phenyl-cyclohexanone derivatives of the general formula I or Ia, also in the form of their diastereomers or enantiomers and of their free bases or of a salt formed with a physiologically tolerated acid, in particular the hydrochloride salt,

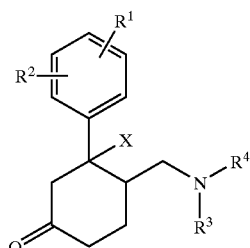

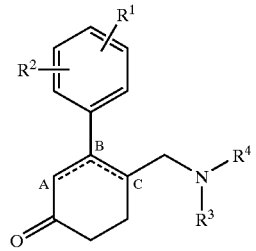

wherein $R^1$ and $R^2$ independently of one another are $R^5$ or $YR^5$, wherein $Y=C_1-C_{10}$-alkyl, $C_2-C_{10}$-alkenyl or $C_2-C_{10}$-alkinyl, branched or unbranched and mono- or polysubstituted or unsubstituted, and wherein $R^5$ is H, F, Cl, Br, I, CN, $NO_2$; $C_1-C_8$-alkyl, $C_2-C_8$-alkenyl or $C_2-C_8$-alkinyl, in each case branched or unbranched and mono- or polysubstituted or unsubstituted; $C_3-C_7$-cycloalkyl, saturated or unsaturated and mono- or polysubstituted or unsubstituted, or a corresponding heterocyclic radical, in which one carbon atom in the ring is replaced by an S, O or $NR^6$, wherein $R^6$ is H; or $C_1-C_{10}$-alkyl, $C_2-C_{10}$-alkenyl or $C_2-C_{10}$-alkinyl, in each case branched or unbranched and mono- or polysubstituted or unsubstituted;

aryl or heteroaryl, in each case mono- or polysubstituted or unsubstituted;

$OR^7$, $OC(O)R^7$, $OC(O)OR^7$, $OC(S)R^7$, $C(O)R^7$, $C(O)OR^7$, $C(S)R^7$, $C(S)OR^7$, $SR^7$, $S(O)R^7$ or $S(O_2)R^7$, wherein $R^7$ is H; or $C_1-C_{18}$-alkyl, $C_2-C_{18}$-alkenyl or $C_2-C_{18}$-alkinyl, in each case branched or unbranched and mono- or polysubstituted or unsubstituted; $C_3-C_7$-cycloalkyl, saturated or unsaturated and mono- or polysubstituted or unsubstituted, or a corresponding heterocyclic radical, in which one carbon atom in the ring is replaced by an S, O or $NR^8$, wherein $R^8$ is H; or $C_1-C_{10}$-alkyl, $C_2-C_{10}$-alkenyl or $C_2-C_{10}$-alkinyl, in each case branched or unbranched and mono- or polysubstituted or unsubstituted;

or alkylaryl, saturated or unsaturated and mono- or polysubstituted or unsubstituted; aryl or heteroaryl, in each case mono- or polysubstituted or unsubstituted; or or NR$^9$R$^{10}$, C(O)NR$^9$R$^{10}$ or S(O$_2$)NR$^9$R$^{10}$, wherein R$^9$ and R$^{10}$ independently of one another are H; or C$_1$–C$_{18}$-alkyl, C$_2$–C$_{18}$-alkenyl or C$_2$–C$_{18}$-alkinyl, in each case branched or unbranched and mono- or polysubstituted or unsubstituted; C$_3$–C$_7$-cycloalkyl, saturated or unsaturated and mono- or polysubstituted or unsubstituted, or a corresponding heterocyclic radical, in which one carbon atom in the ring is replaced by an S, O or NR$^{11}$, wherein R$^{11}$ is H; or C$_1$–C$_{10}$-alkyl, C$_2$–C$_{10}$-alkenyl or C$_2$–C$_{10}$-alkinyl, in each case branched or unbranched and mono- or polysubstituted or unsubstituted;

alkylaryl, saturated or unsaturated and mono- or polysubstituted or unsubstituted; aryl or heteroaryl, in each case mono- or polysubstituted or unsubstituted;

or

R$^9$ and R$^{10}$ together form a C$_3$–C$_7$-cycloalkyl, saturated or unsaturated and mono- or polysubstituted or unsubstituted, or a corresponding heterocyclic radical, in which one carbon atom in the ring is replaced by an S, O or NR$^{12}$, wherein R$^{12}$ is H; or C$_1$–C$_{10}$-alkyl, C$_2$–C$_{10}$-alkenyl or C$_2$–C$_{10}$-alkinyl, in each case branched or unbranched and mono- or polysubstituted or unsubstituted;

or

R$^1$ and R$^2$ together form —CH=CH—CH=CH—, resulting in a naphthyl system which can be mono- or polysubstituted, X is H; F; Cl; Br; I; CF$_3$; O—S(O$_2$)—C$_6$H$_4$-pCH$_3$; or OR$^{13}$ or OC(O)R$^{13}$, wherein R$^{13}$ is H; OR C$_1$–C$_{10}$-alkyl, C$_2$–C$_{10}$-alkenyl or C$_2$–C$_{10}$-alkinyl, in each case branched or unbranched and mono- or polysubstituted or unsubstituted; C$_3$–C$_7$-cycloalkyl, saturated or unsaturated and mono- or polysubstituted or unsubstituted, or a corresponding heterocyclic radical, in which one carbon atom in the ring is replaced by an N, S or O; alkylaryl, saturated or unsaturated and mono- or polysubstituted or unsubstituted; aryl or heteroaryl, in each case mono- or polysubstituted or unsubstituted;

or if according to formula Ia the compound contains no X, a double bond is formed between carbon atoms "A" and "B" or carbon atoms "B" and "C;"

and

R$^3$, R$^4$ independently of one another are

H; or C$_1$–C$_{10}$-alkyl, C$_2$–C$_{10}$-alkenyl or C$_2$–C$_{10}$-alkinyl, in each case branched or unbranched and mono- or polysubstituted or unsubstituted; C$_3$–C$_7$-cycloalkyl, saturated or unsaturated and mono- or polysubstituted or unsubstituted, or a corresponding heterocyclic radical, in which one carbon atom in the ring is replaced by an N, S or O; alkylaryl, saturated or unsaturated and mono- or polysubstituted or unsubstituted; or aryl or heteroaryl, in each case mono- or polysubstituted or unsubstituted;

or

R$^3$ and R$^4$ together form a C$_3$–C$_7$-cycloalkyl, saturated or unsaturated and mono- or polysubstituted or unsubstituted, or a corresponding heterocyclic radical, in which one carbon atom in the ring is replaced by an S, O or NR$^{14}$, wherein R$^{14}$ is H; or C$_1$–C$_{10}$-alkyl, C$_2$–C$_{10}$-alkenyl or C$_2$–C$_{10}$-alkinyl, in each case branched or unbranched and mono- or polysubstituted or unsubstituted.

The following compounds are explicitly excluded from the present invention:

compounds of formula I wherein X=OH, R$^2$=H, R$^3$ and R$^4$=CH$_3$, and R$^1$ is the same as R$^5$, wherein R$^5$=OR$^7$, wherein R$^7$=H, CH$_3$ or an unsubstituted or substituted pyridyl, thienyl, thiazoyl or phenyl group, or R$^5$=OC(O)OR$^7$, wherein R$^7$=C$_1$–C$_5$-alkyl, or R$^5$=OC(O)R$^7$, wherein R$^7$=C$_{1-5}$-alkyl, NH—C$_6$H$_4$—C$_{1-3}$-alkyl, C$_6$H$_4$—OC(O)C$_{1-3}$-alkyl, C$_6$H$_4$—CH$_2$—N(C$_{1-4}$-alkyl)$_2$, C$_6$H$_4$—CH$_2$—(N-4-morpholino) or CHZ'—NHZ," where Z' and Z" are identical or different and are H or C$_{1-6}$-alkyl, compounds of formula I wherein X=H, and compounds of formula Ia wherein a double bond is formed between carbon atom "A" and carbon atom "B," R$^2$=H, R$^3$ and R$^4$=C$_{1-6}$-alkyl, aryl or C$_{3-7}$-cycloalkyl, and R$^1$ at the same time is H, C$_{1-6}$-alkoxy, O—C$_{3-7}$-cycloalkyl, O-aryl or O-heterocyclyl.

In connection with alkyl, alkenyl, alkinyl and cycloalkyl and the "corresponding heterocyclic radical," the term substituted in the context of this invention is understood as meaning the replacement of a hydrogen radical by F, Cl, Br, I, NH$_2$, SH or OH, polysubstituted radicals being understood as meaning radicals which are substituted more than once on different atoms or on the same atom, for example three times on the same carbon atom, as in the case of CF$_3$, or at different places, as in the case of —CH(OH)—CH=CH—CHCl$_2$.

Furthermore, —C(O)— denotes

which also applies to —C(S)— or —S(O)— and —S(O$_2$)—.

The term "C$_1$–C$_8$-alkyl" or "C$_1$–C$_{10}$-alkyl" in the context of this invention denotes hydrocarbons having 1 to 8 or 10 carbon atoms. Examples which may be mentioned are methyl, ethyl, propyl, isopropyl, n-butane, sec-butyl, tert-butyl, n-pentane, neopentyl, n-hexane, n-heptane, n-octane, n-nonane or n-decane.

The term "C$_1$–C$_{18}$-alkyl" in the context of this invention denotes hydrocarbons having 1 to 18 carbon atoms. Examples which may be mentioned are methyl, ethyl, propyl, isopropyl, n-butane, sec-butyl, tert-butyl, n-pentane, neopentyl, n-butane, sec-butyl, n-hexane, n-heptane, n-octane, n-nonane, n-decane, n-undecane, n-dodecane, n-tridecane, n-tetradecane, n-pentadecane, n-hexadecane, n-heptadecane or n-octadecane, unsubstituted or mono or polysubstituted.

The term "C$_2$–C$_{10}$-alkenyl" or "C$_2$–C$_{10}$-alkinyl" or "C$_2$–C$_{18}$-alkenyl" or "C$_2$–C$_{18}$-alkinyl" in the context of this invention denotes hydrocarbons having 2 to 8 or 2 to 18 carbon atoms respectively. Examples which may be mentioned are propenyl, butenyl, pentenyl, hexenyl, heptenyl or octenyl, unsubstituted or mono or polysubstituted, or propinyl, butinyl, pentinyl, hexinyl, heptinyl or octinyl, unsubstituted or mono- or polysubstituted.

The term C$_3$–C$_7$-cycloalkyl in the context of this invention denotes cyclic hydrocarbons having 3 to 7 carbon atoms. Examples which may be mentioned are cyclopropyl, cyclobutyl, cyclopentyl, cyclohexyl, cycloheptyl, cyclohexenyl or cycloheptenyl, saturated or unsaturated and unsubstituted or mono or polysubstituted. In the context of the invention a "corresponding heterocyclic radical" is understood as meaning a C$_3$–C$_7$-cycloalkyl in which one carbon atom in the ring is replaced by anS, O or N. Examples which may be mentioned for this are pyrrolidine, pyran, thiolane, piperidine or tetrahydrofuran.

The term "aryl" in the context of this invention denotes phenyls or naphthyls.

The term "alkylaryl" in the context of this invention denotes aryls substituted by at least $C_1$–$C_{10}$-alkylene, the terms aryl and alkyl having the same meaning as above. In this group benzaryl may be mentioned in particular.

The term "heteroaryl" in the context of this invention denotes 5- or 6-membered aromatic compounds which are optionally provided with a fused-on ring system and contain one or two heteroatoms from the groups consisting of nitrogen, oxygen and/or sulfur. Examples which may be mentioned in this group are furan, thiophene, pyrrole, pyridine, pyrimidine, quinoline, isoquinoline, phthalazine or quinazoline.

In respect of aryl, alkylaryl or heteroaryl, mono- or polysubstituted in the context of this invention is understood as meaning substitution of the ring system by F, Cl, Br, I, $NH_2$, SH, OH, $CF_3$; mono- or polysubstituted or unsubstituted $C_1$–$C_6$-alkyl, $C_1$–$C_6$-alkoxy, $C_2$–$C_8$-alkenyl, $C_2$–$C_8$-alkinyl; or aryl, in particular phenyl; on one or various atoms.

The expression salt formed with a physiologically tolerated acid in the context of this invention is understood as meaning salts of the particular active compound with inorganic or organic acids which are physiologically tolerated—in particular when used in humans and/or mammals. The hydrochloride is particularly preferred.

In a preferred embodiment, aminomethyl-phenyl-cyclohexanone derivatives are compounds according to formula I or Ia wherein $R^1=R^5$, wherein $R^5$ is H; F; Cl; Br; I; $CHF_2$; $CF_3$; $NO_2$; $NH_2$; $C_1$–$C_4$-alkyl or $C_2$–$C_4$-alkenyl, branched or unbranched and mono- or polysubstituted or unsubstituted; aryl, substituted or unsubstituted, $OR^7$, $C(O)OR^7$ or $SR^7$, wherein $R^7$ is
  H; OR $C_1$–$C_4$-alkyl, branched or unbranched and mono- or polysubstituted or unsubstituted; preferably H, $CF_3$ or $CH_3$,
or $S(O_2)NR^9R^{10}$, wherein $R^9$ and $R^{10}$ independently of one another are
  H; OR $C_1$–$C_4$-alkyl, branched or unbranched and mono- or polysubstituted or unsubstituted;
wherein particularly preferably R1=R5, wherein R5 is selected from the group consisting of
  H, F, Cl, OH, $CH_3$, $C_2H_5$, $C_2H_3$, $CHF_2$, $CF_3$, $SCH_3$, $OCF_3$, $OCH_3$, $OC_2H_5$, $C(O)OCH_3$, $C(O)OC_2H_5$ and phenyl, while $R^2$, X, $R^3$ and $R^4$ have one of the meanings already mentioned.

In further preferred aminomethyl-phenyl-cyclohexanone derivatives according to formula I or Ia according to the invention, $R^2=R^5$, wherein $R^5$ is H; F; Cl; Br; I; $SCH_3$; $C_1$–$C_4$-alkyl, $C_2$–$C_4$-alkenyl, branched or unbranched and mono- or polysubstituted or unsubstituted, preferably $CF_3$; $OR^7$, wherein $R^7$ is $C_1$–$C_4$-alkyl, branched or unbranched and mono- or polysubstituted or unsubstituted, preferably $CH_3$;
while $R^1$, X, $R^3$ and $R^4$ have one of the meanings already mentioned.

In further preferred aminomethyl-phenyl-cyclohexanone derivatives according to formula I or Ia according to the invention, $R^1$ and $R^2$ have different meanings or $R^1$ and $R^2$ together form —CH=CH—CH=CH—, resulting in a naphthyl system formed can be mono- or polysubstituted, preferably by halogen, $OC_{1-3}$-alkyl or $C_{1-3}$-alkyl, unsubstitued or mono or polysubstituted, in particular by $OCH_3$.

In another preferred embodiment, aminomethyl-phenyl-cyclohexanone derivatives are compounds according to formula I or Ia wherein X is H; F; Cl; OH; $CF_3$; O—$S(O_2)$—$C_6H_4$-$pCH_3$; or $OC(O)R^7$, wherein $R^7$=H; or $C_1$–$C_4$-alkyl or $C_2$–$C_4$-alkenyl, branched or unbranched and mono- or polysubstituted or unsubstituted,
  preferably X is H; F; Cl; OH; O—$S(O_2)$—$C_6H_4$-$pCH_3$; or $OC(O)R^7$, wherein $R^7$=$C_1$–$C_4$-alkyl, preferably $R^7$=$CH_3$, particularly preferably X=H or OH;
or
if the compound contains no X, according to formula Ia a double bond is formed between carbon atoms "A" and "B" or carbon atoms "B" and "C,"
while $R^1$, $R^2$, $R^3$ and $R^4$ have one of the meanings already mentioned.

In a further embodiment, in the aminomethyl-phenyl-cyclohexanone derivatives according to formula I or Ia, $R^3$ and $R^4$ independently of one another are
  $C_1$–$C_4$-alkyl, branched or unbranched and mono- or polysubstituted or unsubstituted, preferably $CH_3$,
or
$R^3$ and $R^4$ together form a $C_3$–$C_7$-cycloalkyl, saturated or unsaturated and mono- or polysubstituted or unsubstituted,
while $R^1$, $R^2$ and X have one of the meanings already mentioned above.

The invention also provides a process for the preparation of the aminomethyl-phenyl-cyclohexanone derivatives, which are already described as such as being provided by the invention, according to formula Ia, or according to formula I where X=H. According to the process of the present invention, compounds of the formula II

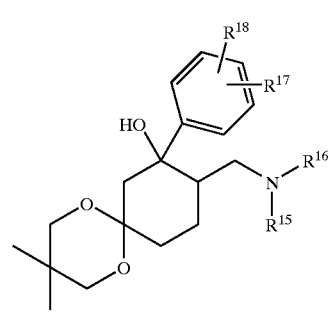

II in which $R^{15}$ has a meaning corresponding to $R^3$, $R^{16}$ to $R^4$ $R^{17}$ to $R^1$ and $R^{18}$ to $R^2$ as already described for formula I and Ia, are reacted with acids, preferably hydrochloric acid, formic acid or acetic acid, at room temperature, to obtain the product according to formula Ia, which is then either purified as the end product, or is hydrogenated with catalytically activated hydrogen to give a product according to formula I where X=H, which is then purified. The hydrogenation is preferably carried out with platinum or palladium as the catalyst absorbed on to a support material, such as active charcoal, in ethyl acetate or a $C_1$–$C_4$-alkyl alcohol, under pressures of 0.1 to 10 bar and/or at temperatures of 20° C. to 80° C.

The invention also provides a process for the preparation of aminomethyl-phenyl-cyclohexanone derivatives accord ing to formula I where X≠H. According to the process of the invention, compounds of formula II

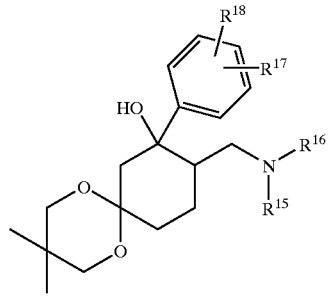

II in which $R^{15}$ has a meaning corresponding to $R^3$, $R^{16}$ to $R^4$, $R^{17}$ to $R^1$ and $R^{18}$ to $R^2$ as already described for formula I and Ia, are reacted with acids, preferably hydrochloric acid, formic acid or acetic acid, at temperatures of between 0° C. and 5° C. The product according to formula 1 where X=OH and $R^{15}$ to $R^{18}$ are unchanged is then either purified as the end product or further processed. If the product is to be converted into a compound where X is F, Cl, Br, I or $CF_3$, the OH group representing X is exchanged for F or Cl or Br or I or $CF_3$ by processes well-known to those of ordinary skill in the art. If the product is to be converted into a compound where X is $OR^{13}$, wherein $R^{13}$ has one of the meanings already described, the OH group representing X is etherified with a halide of formula III

III wherein $R^{19}$ has a meaning according to $R^{13}$ defined above.

If the product is to be converted into a compound where X is O—S($O_2$)—$C_6H_4$—$CH_3$ or OC(O)$R^{13}$, wherein $R^{13}$ has one of the meanings already described, the OH group representing X is esterified with an acid chloride of formula IV

IV or Cl—S($O_2$)—$C_6H_4$—$CH_3$, wherein $R^{20}$ has a meaning analogous to $R^{13}$. Finally, the end product is purified.

The invention also provides a preparation process for starting substances according to formula II of the processes described above. In this, 3,3-dimethyl-1,5-dioxa-spiro[5.5]undecan-8-one

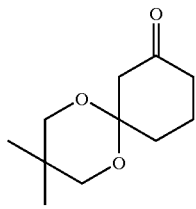

is first reacted with an immonium salt of a compound of formula V or with formaldehyde and an amine of a compound of formula VI, wherein $R^{15}$ has a meaning corresponding to $R^3$ and $R^{16}$ to $R^4$ as already described.

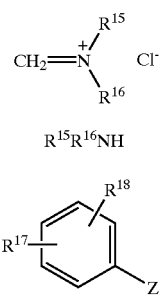

V

VI

VII

The Mannich bases obtained in this way are then reacted with an organometallic compound of formula VII, in which Z denotes MgCl, MgBr, MgI or lithium and $R^{17}$ has a meaning corresponding to $R^1$ and $R^{18}$ to $R^2$ as already described, at temperatures of between −70° C. and 60° C. Preferred solvents in this reaction are diethyl ether or tetrahydrofuran. The reaction with a Grignard compound of the formula VII can be carried out with or without the addition of an entraining reagent. If an entraining reagent is employed, 1,2-dibromoethane is preferred.

Grignard compounds of the formula VII, in which Z denotes MgCl, MgBr or MgI, are commercially obtainable, but can also be prepared by reaction of halogen compounds of the formula VIII, in which A denotes Cl, Br or I and $R^{17}$ has a meaning corresponding to $R^1$ and $R^{18}$ to $R^2$ as already described, with magnesium. Organolithium compounds of the formula VII, in which Z denotes Li, can be obtained by halogen-lithium exchange by reacting halogen compounds of the formula VIII, in which A denotes Cl, Br or I, with, for example, n-butyllithium/hexane solution.

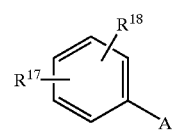

VIII

Because OH, SH and $NH_2$ groups can undergo undesirable side reactions under the reaction conditions mentioned, it is therefore preferable to protect these groups, or in the case of $NH_2$ to replace it by $NO_2$, and to remove the protective group or reduce the $NO_2$ group in the last reaction step before purification. The Application therefore also provides a modification of the processes described above, in which in $R^{15}$ to $R^{20}$ according to formulae II to VII, and optionally also VIII, at least one OH group has been replaced by an OSi(Ph)$_2$tert-but group, at least one SH group has been replaced by an S-p-methoxybenzyl group and/or at least one $NH_2$ group has been replaced by an $NO_2$ group and, after conclusion of the entire reaction sequence, before purification of the end product, an OSi(Ph)$_2$tert-but group is removed with tetrabutylammonium fluoride in tetrahydrofuran and/or at least one p-methoxybenzyl group is removed with a metal amine, preferably sodium amine, and/or at least one $NO_2$ group is reduced to $NH_2$.

Furthermore, carboxylic acid or thiocarboxylic acid groups are not stable under certain circumstances under the reaction conditions mentioned, so that it is preferable to react methyl esters thereof and to hydrolyze the process product with KOH solution or NaOH solution in methanol at 40° C. −60° C. after conclusion of the entire reaction sequence, before the purification. The invention therefore also provides a modification of the processes described above in which, after conclusion of the entire reaction sequence, before the purification of the end product, a process product with at least one C(O)OCH$_3$, OC(O)OCH$_3$ and/or C(S)OCH$_3$ group is hydrolyzed with KOH solution or NaOH solution in methanol at 40° C.–60° C.

The purification of the compounds obtained in the individual reaction sequences is carried out by crystallization or column chromatography.

The compounds of the formula I or Ia can be converted into their salts, in a manner well-known to those of ordinary skills in the art; physiologically tolerated acids, such as hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. The salt formation is preferably carried out in a solvent, such as diisopropyl ether, acetic acid alkyl esters, acetone and/or 2-butanone. Trimethylchlorosilane in aqueous solution is particularly suitable for preparation of the hydrochlorides.

The aminomethyl-phenyl-cyclohexanone derivatives according to the invention are toxicologically acceptable, so that they are suitable as the pharmaceutical active compound in medicaments.

The invention therefore also provides medicaments which comprise, as the active compound, at least one aminomethyl-phenyl-cyclohexanone derivative of the general formula I or Ia

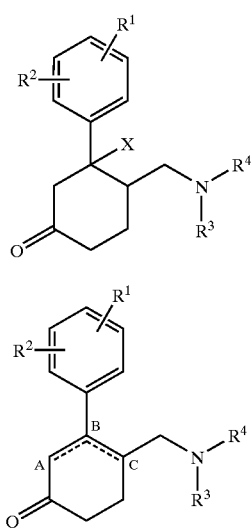

wherein
R$^1$ and R$^2$ independently of one another are R$^5$ or YR$^5$, where Y is C$_1$–C$_{10}$-alkyl, C$_2$–C$_{10}$-alkenyl or C$_2$–C$_{10}$-alkinyl, branched or unbranched and mono- or polysubstituted or unsubstituted, wherein R$^5$ is
H; F; Cl; Br; I; CN; NO$_2$; C$_1$–C$_8$-alkyl, C$_2$–C$_8$-alkenyl or C$_2$–C$_8$-alkinyl, in each case branched or unbranched and mono- or polysubstituted or unsubstituted; C$_3$–C$_7$-cycloalkyl, saturated or unsaturated and mono- or polysubstituted or unsubstituted, or a corresponding heterocyclic radical, in which one carbon atom in the ring is replaced by an S, O or NR$^6$, wherein R$^6$ is
H; or C$_1$–C$^{10}$-alkyl, C$_2$–C$_{10}$-alkenyl or C$_2$–C$_{10}$-alkinyl, in each case branched or unbranched and mono- or polysubstituted or unsubstituted;

aryl or heteroaryl, in each case mono- or polysubstituted or unsubstituted;
OR$^7$, OC(O)R$^7$, OC(O)OR$^7$, OC(S)R$^7$, C(O)R$^7$, C(O)OR$^7$, C(S)R$^7$, C(S)OR$^7$, SR$^7$, S(O)R$^7$ or S(O$_2$)R$^7$, wherein R$^7$ is
H; or C$_1$–C$_{18}$-alkyl, C$_2$–C$_{18}$-alkenyl or C$_2$–C$_{18}$-alkinyl, in each case branched or unbranched and mono- or polysubstituted or unsubstituted; C$_3$–C$_7$-cycloalkyl, saturated or unsaturated and mono- or polysubstituted or unsubstituted, or a corresponding heterocyclic radical, in which one carbon atom in the ring is replaced by an S, O or NR$^8$, wherein R$^8$ is
H; or C$_1$–C$_{10}$-alkyl, C$_2$–C$_{10}$-alkenyl or C$_2$–C$_{10}$-alkinyl, in each case branched or unbranched and mono- or polysubstituted or unsubstituted;
or alkylaryl, saturated or unsaturated and mono- or polysubstituted or unsubstituted; aryl or heteroaryl, in each case mono- or polysubstituted or unsubstituted;
or
NR$^9$R$^{10}$, C(O)NR$^9$R$^{10}$ or S(O$_2$)NR$^9$R$^{10}$, wherein R$^9$ and R$^{10}$ independently of one another are
H; or C$_1$–C$_{18}$-alkyl, C$_2$–C$_{18}$-alkenyl or C$_2$–C$_{18}$-alkinyl, in each case branched or unbranched and mono- or polysubstituted or unsubstituted; C$_3$–C$_7$-cycloalkyl, saturated or unsaturated and mono- or polysubstituted or unsubstituted, or a corresponding heterocyclic radical, in which one carbon atom in the ring is replaced by an S, O or NR$^{11}$, wherein R$^{11}$ is
H; or C$_1$–C$_{10}$-alkyl, C$_2$–C$_{10}$-alkenyl or C$_2$–C$_{10}$-alkinyl, in each case branched or unbranched and mono- or polysubstituted or unsubstituted;
or alkylaryl, saturated or unsaturated and mono- or polysubstituted or unsubstituted; aryl or heteroaryl, in each case mono- or polysubstituted or unsubstituted;
or
R$^9$ and R$^{10}$ together form a C$_3$–C$_7$-cycloalkyl, saturated or unsaturated and mono- or polysubstituted or unsubstituted, or a corresponding heterocyclic radical, in which one carbon atom in the ring is replaced by an S, O or NR$^{12}$, wherein R$^{12}$ is
H; or C$_1$–C$_{10}$-alkyl, C$_2$–C$_{10}$-alkenyl or C$_2$–C$_{10}$-alkinyl, in each case branched or unbranched and mono- or polysubstituted or unsubstituted;
or
R$^1$ and R$^2$ together form —CH=CH—CH=CH—, wherein the naphthyl system formed can be mono- or polysubstituted,
X is
H; F; Cl; Br; I; CF$_3$; O—S(O$_2$)—C$_6$H$_4$-pCH$_3$, or OR$^{13}$ or OC(O)R$^{13}$, wherein R$^{13}$ is
H; OR C$_1$–C$_{10}$-alkyl, C$_2$–C$_{10}$-alkenyl or C$_2$–C$_{10}$-alkinyl, in each case branched or unbranched and mono- or polysubstituted or unsubstituted; or C$_3$–C$_7$-cycloalkyl, saturated or unsaturated and mono- or polysubstituted or unsubstituted, or a corresponding heterocyclic radical, in which one carbon atom in the ring is replaced by an N, S or O; alkylaryl, saturated or unsaturated and mono- or polysubstituted or unsubstituted; aryl or heteroaryl, in each case mono- or polysubstituted or unsubstituted;
or
if according to formula Ia the compound contains no X, a double bond is formed between carbon atoms "A" and "B" or carbon atoms "B" and "C;"

and

R³, R⁴ independently of one another are
H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by an N, S or O; alkylaryl, saturated or unsaturated and mono- or polysubstituted or unsubstituted; or aryl or heteroaryl, in each case mono- or polysubstituted or unsubstituted;
or R³ and R⁴ together form a $C_3$–$C_7$-cycloalkyl, saturated or unsaturated and mono- or polysubstituted or unsubstituted, or a corresponding heterocyclic radical, in which one carbon atom in the ring is replaced by an S, O or $NR^{14}$, wherein $R^{14}$ is
H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;

in the form of its diastereomers or enantiomers and of its free base or of a salt formed with a physiologically tolerated acid, in particular the hydrochloride salt.

Preferred medicaments are those comprising at least one aminomethyl-phenyl-cyclohexanone derivative of the general formula I or Ia

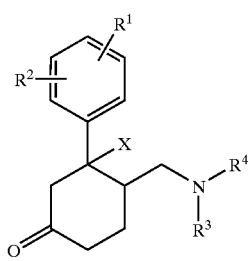

I

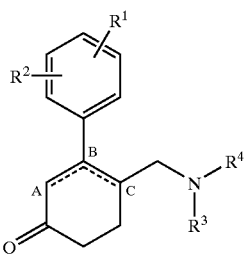

Ia in which, independently of one another
$R^1$=$R^5$, wherein $R^5$ is
H; F; Cl; Br; I; $CHF_2$; $CF_3$; $NO_2$; $NH_2$; $C_1$–$C_4$-alkyl or $C_2$–$C_4$-alkenyl, branched or unbranched and mono- or polysubstituted or unsubstituted; aryl, substituted or unsubstituted; $OR^7$, $C(O)OR^7$ or $SR^7$, wherein $R^7$ is
H; or $C_1$–$C_4$-alkyl, branched or unbranched and mono- or polysubstituted or unsubstituted; preferably H, $CF_3$ or $CH_3$,
or $S(O_2)NR^9R^{10}$, wherein $R^9$ and $R^{10}$ independently of one another are
H; OR $C_1$–$C_4$-alkyl, branched or unbranched and mono- or polysubstituted or unsubstituted;
wherein particularly preferably R1=R5, wherein R5 is
H, F, Cl, OH, $CH_3$, $C_2H_5$, $C_2H_3$, $CHF_2$, $CF_3$, $SCH_3$, $OCF_3$, $OCH_3$, $OC_2H_5$, $C(O)OCH_3$, or $C(O)OC_2H_5$, or phenyl and/or $R^2$=$R^5$, wherein $R^5$ is
H; F; Cl; Br; I; $SCH_3$; $C_1$–$C_4$-alkyl, $C_2$–$C_4$-alkenyl, branched or unbranched and mono- or polysubstituted or unsubstituted, preferably $CF_3$; $OR^7$, wherein $R^7$ is $C_1$–$C_4$-alkyl, branched or unbranched and mono- or polysubstituted or unsubstituted, preferably $CH_3$;
and/or $R^1$ and $R^2$ have different meanings or $R^1$ and $R^2$ together form —CH═CH—CH═CH—, resulting in a naphthyl system which is mono- or polysubstituted, preferably by halogen; or by $OC_{1-3}$-alkyl or $C_{1-3}$-alkyl, unsubstituted or mono or polysubstituted, in particular by $OCH_3$;
and/or X is
H; F; Cl; OH; $CF_3$; O—$S(O_2)$—$C_6H_4$-$pCH_3$ or OC(O)$R^7$, wherein $R^7$=H; or $C_1$–$C_4$-alkyl or $C_2$–$C_4$-alkenyl,
branched or unbranched and mono- or polysubstituted or unsubstituted,
preferably H, F, Cl, OH, O—$S(O_2)$—$C_6H_4$-$pCH_3$ or OC(O)$R^7$, wherein $R^7$=$C_1$–$C_4$-alkyl, preferably $CH_3$, in particular H or OH;
or
if according to formula Ia the compound contains no X, a double bond is formed between carbon atoms "A" and "B" or carbon atoms "B" and "C,"
and/or R³ and R⁴ independently of one another are
$C_1$–$C_4$-alkyl, branched or unbranched and mono- or polysubstituted or unsubstituted, preferably $CH_3$;
or
R³ and R⁴ together form a $C_3$–$C_7$-cycloalkyl, saturated or unsaturated and mono- or polysubstituted or unsubstituted,
and/or $R^1$, $R^2$, X, $R^3$ and/or $R^4$ have one of the meanings already mentioned.

Particularly preferred medicaments according to the present invention are those which comprise as the active compound at least one aminomethyl-phenyl-cyclohexanone derivative selected from the group consisting of:
rac-cis-[4-dimethylaminomethyl-3-hydroxy-3-(3-methoxy-phenyl)-cyclohexanone];
rac-cis-[4-dimethylaminomethyl-3-(3-methoxy-phenyl)-cyclohexanone];
rac-trans-[4-dimethylaminomethyl-3-(3-methoxy-phenyl)-cyclohexanone];
rac-cis-[4-dimethylaminomethyl-3-(3-hydroxy-phenyl)-cyclohexanone];
rac-trans-[4-dimethylaminomethyl-3-(3-hydroxy-phenyl)-cyclohexanone];
4-dimethylaminomethyl-3-(3-methoxy-phenyl)-cyclohex-2-enone;
4-dimethylaminomethyl-3-phenyl-cyclohex-2-enone;
4-dimethylaminomethyl-3-(3-hydroxy-phenyl)-cyclohex-2-enone;
rac-trans-4-dimethylaminomethyl-3-phenyl-cyclohexanone;
rac-cis-4-dimethylaminomethyl-3-phenyl-cyclohexanone;
4-dimethylaminomethyl-3-(4-methoxy-phenyl)-cyclohex-2-enone;
4-dimethylaminomethyl-3-naphthalen-2-yl-cyclohex-2-enone;
rac-trans-4-dimethylaminomethyl-3-hydroxy-3-naphthalen-2-yl-cyclohexanone;
rac-trans-4-dimethylaminomethyl-3-(3-fluoro-phenyl)-cyclohexanone;
rac-cis-4-dimethylaminomethyl-3-(3-fluoro-phenyl)-cyclohexanone;
rac-cis-4-dimethylaminomethyl-3-hydroxy-3-(2-methoxy-phenyl)-cyclohexanone;

rac-cis-4-dimethylaminomethyl-3-hydroxy-3-(6-methoxy-naphthalen-2-yl)-cyclohexanone;
4-dimethylaminomethyl-3-(6-methoxy-naphthalen-2-yl)-cyclohex-2-enone;
rac-cis-3-biphenyl-4-yl-4-dimethylaminomethyl-3-hydroxy-cyclohexanone;
3-(3-difluoromethyl-phenyl)-4-dimethylaminomethyl-cyclohex-2-enone;
4-dimethylaminomethyl-3-(3-fluoro-phenyl)-cyclohex-2-enone;
3-(3,4-difluoro-phenyl)-4-dimethylaminomethyl-cyclohex-2-enone;
4-dimethylaminomethyl-3-(4-fluoro-phenyl)-cyclohex-2-enone;
4-dimethylaminomethyl-3-(4-trifluoromethyl-phenyl)-cyclohex-2-enone;
3-(3,5-dichloro-phenyl)-4-dimethylaminomethyl-cyclohex-2-enone;
3-(3,5-difluoro-phenyl)-4-dimethylaminomethyl-cyclohex-2-enone; and
rac-cis-3-(3,5-difluoro-phenyl)-4-dimethylaminomethyl-3-hydroxy-cyclohexanone, as the free base or in the form of a salt formed with a physiologically tolerated acid, in particular the hydrochloride salt.

Medicaments according to the invention comprise, in addition to at least one aminomethyl-phenyl-cyclohexanone derivative, pharmaceutically acceptable excipients such as carrier materials, fillers, solvents, diluents, dyestuffs and/or binders, and can be administered as liquid medicament forms in the form of injection solutions, drops or juices, or as semi-solid medicament forms in the form of granules, tablets, pellets, patches, capsules, plasters or aerosols. The choice of auxiliary substances and the amounts thereof to be employed depend on whether the medicament is to be administered orally, perorally, parenterally, intravenously, intraperitoneally, intradermally, intramuscularly, intranasally, buccally, rectally or locally, for example on infections of the skin, the mucous membranes and the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Aminomethyl-phenyl-cyclohexanone derivatives according to the invention in a depot in dissolved form or in a patch, optionally with the addition of agents which promote penetration through the skin, are suitable formulations for percutaneous administration. Formulation forms which can be used orally or percutaneously can release the aminomethyl-phenyl-cyclohexanone derivatives in a delayed manner. The amount of active compound to be administered to the patient varies according to the weight of the patient, the mode of administration, and the indication and the severity of the disease. 50 to 500 mg/kg of at least one aminomethyl-phenyl-cyclohexanone derivative are usually administered.

The aminomethyl-phenyl-cyclohexanone derivatives are preferably employed for treatment of pain. Accordingly, the invention also provides the use of at least one aminomethyl-phenyl-cyclohexanone derivative of the general formula I or Ia

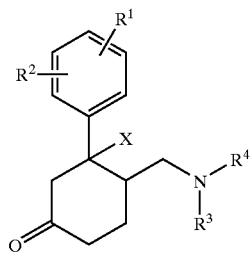

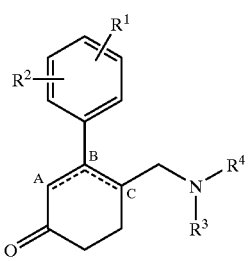

wherein
$R^1$ and $R^2$ independently of one another are $R^5$ or $YR^5$, wherein Y is $C_1$–$C_{10}$-alkyl, $C_2$–$C_{10}$-alkenyl or $C_2$–$C_{10}$-alkinyl, branched or unbranched and mono- or polysubstituted or unsubstituted, wherein $R^5$ is
H; F; Cl; Br; I; CN; $NO_2$; $C_1$–$C_8$-alkyl, $C_2$–$C_8$-alkenyl or $C_2$–$C_8$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by an S, O or $NR^6$, wherein $R^6$ is
H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;
aryl or heteroaryl, in each case mono- or polysubstituted or unsubstituted;
$OR^7$, $OC(O)R^7$, $OC(O)OR^7$, $OC(S)R^7$, $C(O)R^7$, $C(O)OR^7$, $C(S)R^7$, $C(S)OR^7$, $SR^7$, $S(O)R^7$ or $S(O_2)R^7$, wherein $R^7$ is
H; or $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by an S, O or $NR^8$, wherein $R^8$ is
H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;
or alkylaryl, saturated or unsaturated and mono- or polysubstituted or unsubstituted; aryl or heteroaryl, in each case mono- or polysubstituted or unsubstituted;
or
$NR^9R^{10}$, $C(O)NR^9R^{10}$ or $S(O_2)NR^9R^{10}$, wherein $R^9$ and $R^{10}$ independently of one another are
H; or $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by an S, O or $NR^{11}$, wherein $R^{11}$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;
or alkylaryl, saturated or unsaturated and mono- or polysubstituted or unsubstituted; aryl or heteroaryl, in each case mono- or polysubstituted or unsubstituted;

or $R^9$ and $R^{10}$ together form a $C_3$–$C_7$-cycloalkyl, saturated or unsaturated and mono- or polysubstituted or unsubstituted, or a corresponding heterocyclic radical, in which one carbon atom in the ring is replaced by an S, O or $NR^{12}$ wherein $R^{12}$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;

or $R^1$ and $R^2$ together form —CH=CH—CH=CH—, resulting in a naphthyl system which can be mono- or polysubstituted, X is H; F; Cl; Br; I; $CF_3$; O—$S(O_2)$—$C_6H_4$-$pCH_3$, or $OR^{13}$ or $OC(O)R^{13}$, wherein $R^{13}$ is H; OR, $C_1$–$C_{10}$-alkyl, $C_2$–$C_{10}$-alkenyl or $C_2$–$C_{10}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by an N, S or O; or alkylaryl, saturated or unsaturated and mono- or polysubstituted or unsubstituted; aryl or heteroaryl, in each case mono- or polysubstituted or unsubstituted;

or if according to formula Ia the compound contains no X, a double bond is formed between carbon atoms "A" and "B" or carbon atoms "B" and "C;"

and $R^3$, $R^4$ independently of one another are

H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by an N, S or O; alkylaryl, saturated or unsaturated and mono- or polysubstituted or unsubstituted; or aryl or heteroaryl, in each case mono- or polysubstituted or unsubstituted;

or $R^3$ and $R^4$ together form a $C_3$–$C_7$-cycloalkyl, saturated or unsaturated and mono- or polysubstituted or unsubstituted, or a corresponding heterocyclic radical, in which one carbon atom in the ring is replaced by an S, O or $NR^{14}$, wherein $R^{14}$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;
in the form of its diastereomers or enantiomers and of its free base or of a salt formed with a physiologically tolerated acid, in particular the hydrochloride salt, for the preparation of a medicament for treatment of pain.

It has been found, surprisingly, that the aminomethyl-phenyl-cyclohexanone derivatives according to the invention are very suitable for further indications, in particular for treatment of urinary incontinence, itching and/or diarrhoea, and also in other indications. The Application therefore also provides the use of at least one aminomethyl-phenyl-cyclohexanone derivative of the general formula I or Ia

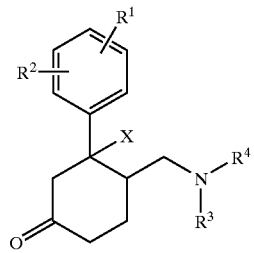

I

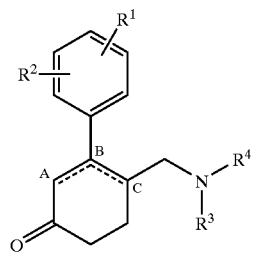

Ia wherein $R^1$ and $R^2$ independently of one another are $R^5$ or $YR^5$, wherein Y is $C_1$–$C_{10}$-alkyl, $C_2$–$C_{10}$-alkenyl or $C_2$–$C_{10}$-alkinyl, branched or unbranched and mono- or polysubstituted or unsubstituted, wherein $R^5$ is H; F; Cl; Br; I; CN; $NO_2$; $C_1$–$C_8$-alkyl, $C_2$–$C_8$-alkenyl or $C_2$–$C_8$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by an S, O or $NR^6$, wherein $R^6$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;
aryl or heteroaryl, in each case mono- or polysubstituted or unsubstituted;
$OR^7$, $OC(O)R^7$, $OC(O)OR^7$, $OC(S)R^7$, $C(O)R^7$ $C(O)OR^7$, $C(S)R^7$, $C(S)OR^7$, $SR^7$, $S(O)R^7$ or $S(O_2)R^7$, wherein $R^7$ is H; or $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by an S, O or $NR^8$, wherein $R^8$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;
alkylaryl, saturated or unsaturated and mono- or polysubstituted or unsubstituted; aryl or heteroaryl, in each case mono- or polysubstituted or unsubstituted; or
$NR^9R^{10}$, $C(O)NR^9R^{10}$ or $S(O_2)NR^9R^{10}$, wherein $R^9$ and $R^{10}$ independently of one another are H; or $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3–C_7$-cycloalkyl, saturated or unsaturated and mono- or polysubstituted or unsubstituted, or a corresponding heterocyclic radical, in which one carbon atom in the ring is replaced by an S, O or $NR^{11}$, wherein $R^{11}$ is H; or $C_1–C_{10}$-alkyl, $C_2–C_{10}$-alkenyl or $C_2–C_{10}$-alkinyl, in each case branched or unbranched and mono- or polysubstituted or unsubstituted; or alkylaryl, saturated or unsaturated and mono- or polysubstituted or unsubstituted; aryl or heteroaryl, in each case mono- or polysubstituted or unsubstituted;

or $R^9$ and $R^{10}$ together form a $C_3–C_7$-cycloalkyl, saturated or unsaturated and mono- or polysubstituted or unsubstituted, or a corresponding heterocyclic radical, in which one carbon atom in the ring is replaced by an S, O or $NR^{12}$, wherein $R^{12}$ is H; or $C_1–C_{10}$-alkyl, $C_2–C_{10}$-alkenyl or $C_2–C_{10}$-alkinyl, in each case branched or unbranched and mono- or polysubstituted or unsubstituted;

or $R^1$ and $R^2$ together form —CH=CH—CH=CH—, resulting in a naphthyl system which can be mono- or polysubstituted, X is H; F; Cl; Br; I; $CF_3$; O—$S(O_2)$—$C_6H_4$-$pCH_3$, $OR^{13}$ or $OC(O)R^{13}$, wherein $R^{13}$ is H; OR $C_1–C_{10}$-alkyl, $C_2–C_{10}$-alkenyl or $C_2–C_{10}$-alkinyl, in each case branched or unbranched and mono- or polysubstituted or unsubstituted; or $C_3–C_7$-cycloalkyl, saturated or unsaturated and mono- or polysubstituted or unsubstituted, or a corresponding heterocyclic radical, in which one carbon atom in the ring is replaced by an N, S or O; alkylaryl, saturated or unsaturated and mono- or polysubstituted or unsubstituted; aryl or heteroaryl, in each case mono- or polysubstituted or unsubstituted;

or if according to formula Ia the compound contains no X, a double bond is formed between carbon atoms "A" and "B" or carbon atoms "B" and "C;"

and $R^3$, $R^4$ independently of one another are

H; or $C_1–C_{10}$-alkyl, $C_2–C_{10}$-alkenyl or $C_2–C_{10}$-alkinyl, in each case branched or unbranched and mono- or polysubstituted or unsubstituted; or $C_3–C_7$-cycloalkyl, saturated or unsaturated and mono- or polysubstituted or unsubstituted, or a corresponding heterocyclic radical, in which one carbon atom in the ring is replaced by an N, S or O ; alkylaryl, saturated or unsaturated and mono- or polysubstituted or unsubstituted; aryl or heteroaryl, in each case mono- or polysubstituted or unsubstituted;

or $R^3$ and $R^4$ together form a $C_3–C_7$-cycloalkyl, saturated or unsaturated and mono- or polysubstituted or unsubstituted, or a corresponding heterocyclic radical, in which one carbon atom in the ring is replaced by an S, O or $NR^{14}$, wherein $R^{14}$ is H; or $C_1–C_{10}$-alkyl, $C_2–C_{10}$-alkenyl or $C_2–C_{10}$-alkinyl, in each case branched or unbranched and mono- or polysubstituted or unsubstituted;

in the form of its diastereomers or enantiomers and of its free base or of a salt formed with a physiologically tolerated acid, in particular the hydrochloride salt, for the preparation of a medicament for treatment of inflammatory and allergic reactions, depressions, drug and/or alcohol abuse, gastritis, cardiovascular diseases, respiratory tract diseases, coughing, mental illnesses and/or epilepsy, and in particular urinary incontinence, itching and/or diarrhoea.

The use of at least preferred aminomethyl-phenyl-cyclohexanone derivatives for the above uses are compounds according to formula I or Ia

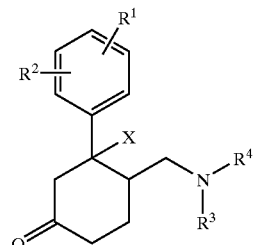

I

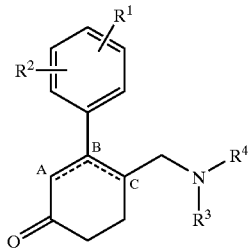

Ia in which, independently of one another $R^1=R^5$, wherein $R^5$ is

H; F; Cl; Br; I; $CHF_2$; $CF_3$; $NO_2$; $NH_2$; $C_1–C_4$-alkyl or $C_2–C_4$-alkenyl, branched or unbranched and mono- or polysubstituted or unsubstituted; aryl, substituted or unsubstituted; $OR^7$, $C(O)OR^7$ or $SR^7$, wherein $R^7$ is H; OR $C_1–C_4$-alkyl, branched or unbranched and mono- or polysubstituted or unsubstituted; preferably H, $CF_3$ or $CH_3$, or $S(O_2)NR^9R^{10}$, wherein $R^9$ and $R^{10}$ independently of one another are H; OR $C_1–C_4$-alkyl, branched or unbranched and mono- or polysubstituted or unsubstituted;

wherein particularly preferably R1=R5, wherein R5 is

H, F, Cl, OH, $CH_3$, $C_2H_5$, $C_2H_3$, $CHF_2$, $CF_3$, $SCH_3$, $OCF_3$, $OCH_3$, $OC_2H_5$, $C(O)OCH_3$, $C(O)OC_2H_5$ or phenyl, and/or $R^2=R^5$, wherein $R^5$ is H; F; Cl; Br; I; $SCH_3$; $C_1–C_4$-alkyl or $C_2–C_4$-alkenyl, branched or unbranched and mono- or polysubstituted or unsubstituted, preferably $CF_3$; $OR^7$, wherein $R^7$ is $C_1–C_4$-alkyl, branched or unbranched and mono- or polysubstituted or unsubstituted, preferably $CH_3$;

and/or $R^1$ and $R^2$ have different meanings, or $R^1$ and $R^2$ together form —CH=CH—CH=CH—, resulting in a naphthyl system which can be mono- or polysubstituted, preferably by halogen, $OC_{1-3}$-alkyl or $C_{1-3}$-alkyl, unsubstituted or mono or polysubstituted, in particular by $OCH_3$, and/or X is H; F; Cl ; OH; $CF_3$; O—$S(O_2)$—$C_6H_4$-$pCH_3$ or $OC(O)R^7$, wherein $R^7=H$; or $C_1–C_4$-alkyl or $C_2–C_4$-alkenyl, branched or unbranched and mono- or polysubstituted or unsubstituted;

preferably X is H, F, Cl, OH, O—S(O$_2$)—C$_6$H$_4$-pCH$_3$; OC(O)R$^7$, wherein R$^7$=C$_1$–C$_4$-alkyl, preferably CH$_3$, in particular X is H or OH;
or
if according to formula Ia the compound contains no X, a double bond is formed between carbon atoms "A" and "B" or carbon atoms "B" and "C,"
and/or R$^3$ and R$^4$ independently of one another are
C$_1$–C$_4$-alkyl, branched or unbranched and mono- or polysubstituted or unsubstituted, preferably CH$_3$;
or
R$^3$ and R$^4$ together form a C$_3$–C$_7$-cycloalkyl, saturated or unsaturated and mono- or polysubstituted or unsubstituted,
and/or R$^1$, R$^2$, X, R$^3$ and/or R$^4$ have one of the meanings already given.

The use of at least one particularly preferred aminomethyl-phenyl-cyclohexanone derivatives for the use to treat the above diseases are the compounds selected from the group consisting of rac-cis-[4-dimethylaminomethyl-3-hydroxy-3-(3-methoxy-phenyl)-cyclohexanone];
rac-cis-[4-dimethylaminomethyl-3-(3-methoxy-phenyl)-cyclohexanone];
rac-trans-[4-dimethylaminomethyl-3-(3-methoxy-phenyl)-cyclohexanone];
rac-cis-[4-dimethylaminomethyl-3-(3-hydroxy-phenyl)-cyclohexanone];
rac-trans-[4-dimethylaminomethyl-3-(3-hydroxy-phenyl)-cyclohexanone];
4-dimethylaminomethyl-3-(3-methoxy-phenyl)-cyclohex-2-enone;
4-dimethylaminomethyl-3-phenyl-cyclohex-2-enone;
4-dimethylaminomethyl-3-(3-hydroxy-phenyl)-cyclohex-2-enone;
rac-trans-4-dimethylaminomethyl-3-phenyl-cyclohexanone;
rac-cis-4-dimethylaminomethyl-3-phenyl-cyclohexanone;
4-dimethylaminomethyl-3-(4-methoxy-phenyl)-cyclohex-2-enone;
4-dimethylaminomethyl-3-naphthalen-2-yl-cyclohex-2-enone;
rac-trans-4-dimethylaminomethyl-3-hydroxy-3-naphthalen-2-yl-cyclohexanone;
rac-trans-4-dimethylaminomethyl-3-(3-fluoro-phenyl)-cyclohexanone;
rac-cis-4-dimethylaminomethyl-3-(3-fluoro-phenyl)-cyclohexanone;
rac-cis-4-dimethylaminomethyl-3-hydroxy-3-(2-methoxy-phenyl)-cyclohexanone;
rac-cis-4-dimethylaminomethyl-3-hydroxy-3-(6-methoxy-naphthalen-2-yl)-cyclohexanone;
4-dimethylaminomethyl-3-(6-methoxy-naphthalen-2-yl)-cyclohex-2-enone;
rac-cis-3-biphenyl-4-yl-4-dimethylaminomethyl-3-hydroxy-cyclohexanone;
3-(3-difluoromethyl-phenyl)-4-dimethylaminomethyl-cyclohex-2-enone;
4-dimethylaminomethyl-3-(3-fluoro-phenyl)-cyclohex-2-enone;
3-(3;4-difluoro-phenyl)-4-dimethylaminomethyl-cyclohex-2-enone;
4-dimethylaminomethyl-3-(4-fluoro-phenyl)-cyclohex-2-enone;
4-dimethylaminomethyl-3-(4-trifluoromethyl-phenyl)-cyclohex-2-enone;
3-(3;5-dichloro-phenyl)-4-dimethylaminomethyl-cyclohex-2-enone;
3-(3;5-difluoro-phenyl)-4-dimethylaminomethyl-cyclohex-2-enone; and
rac-cis-3-(3;5-difluoro-phenyl)-4-dimethylaminomethyl-3-hydroxy-cyclohexanone;

as their free bases or in the form of a salt formed with a physiologically tolerated acid, in particular the hydrochloride salt.

The invention is explained further by examples in the following, without limiting it thereto.

EXAMPLES

The following examples show compounds according to the invention and the preparation thereof, and activity studies carried out therewith.

The following information generally applies:

The yields of the compounds prepared are not optimized.

All temperatures are uncorrected.

Silica gel 60 (0.040–0.063 mm) from E. Merck, Darmstadt was employed as the stationary phase for the column chromatography.

The thin layer chromatography studies were carried out with HPTLC precoated plates, silica gel 60 F 254 from E. Merck, Darmstadt.

The mixing ratios of the mobile phases for all the chromatographic studies are always stated in volume/volume.

The term ether means diethyl ether.

Unless stated otherwise, petroleum ether with the boiling range of 50° C.–70° C. was used.

Example 1 rac-cis-[4-Dimethylaminomethyl-3-hydroxy-3-(3-methoxy-phenyl)-cyclohexanone](compound 1) and 4-dimethylaminomethyl-3-(3-methoxy-phenyl)-cyclohex-2-enone (compound 6)

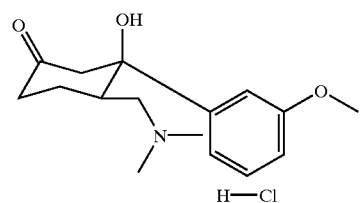

(1)

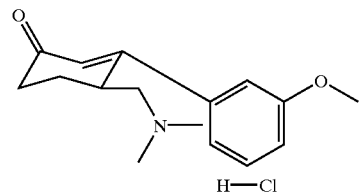

(6)

Stage 1

3,3-Dimethyl-1,5-dioxa-spiro[5.5]undecan-8-one

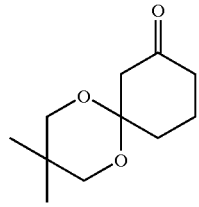

448.5 g 1,3-cyclohexanedione, 416 g 2,2-dimethyl-1,3-propanediol and 12 g p-toluenesulfonic acid were introduced into 3,000 ml methylene chloride and the mixture was heated under reflux for 24 hours using a water separator. When the reaction had ended the mixture was cooled to room temperature and 2,000 ml 32% sodium hydroxide solution were added. The phases were separated and the organic phase was washed first with sodium bicarbonate solution (44.4 g sodium bicarbonate solution/850 ml water) and then with 350 ml water. The organic phase was dried over sodium sulfate and the solvent was then evaporated in vacuo. 345 g (50% of theory) 3,3-dimethyl-1,5-dioxa-spiro[5.5]undecan-8-one were obtained in this way.

Stage 2

9-Dimethylaminomethyl-3,3-dimethyl-1,5-dioxa-spiro[5.5]undecan-8-one

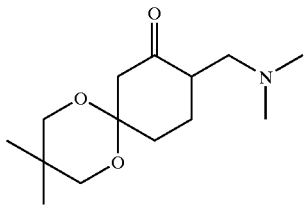

345 g 3,3-dimethyl-3,3-dimethyl-1,5-dioxa-spiro[5.5]undecan-8-one were dissolved in 1,900 ml analytical grade acetonitrile. The mixture was cooled to 0° C. and 140 g N,N-dimethylmethylene-immonium chloride and one drop of acetyl chloride were then added. The mixture was stirred at 0° C. for 6 hours. The reaction mixture was left overnight at room temperature. The white solid which had precipitated out was filtered off with suction, washed with acetone and dried in vacuo. 310 g 9-dimethylaminomethyl-1,5-dioxa-spiro[5.5]undecan-8-one hydrochloride were obtained in this way as a white solid. To liberate the base, the solid was dissolved in water, and an equimolar amount of saturated sodium carbonate solution was added. The mixture was stirred for one hour. The mixture was extracted 3 times with 500 ml ethyl acetate. The combined organic phases were dried over sodium sulfate and the solvent was evaporated in vacuo. 300 g (68% of theory) 9-dimethylaminomethyl-1,5-dioxa-spiro[5.5]undecan-8-one were obtained in this way.

Stage 3

9-Dimethylaminomethyl-8-(3-methoxy-phenyl)-3,3-dimethyl-1,5-dioxa-spiro[5.5]undecan-8-ol

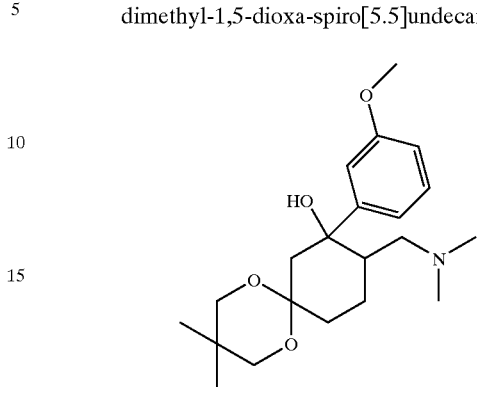

36 g magnesium were initially introduced into 150 ml analytical grade tetrahydrofuran. 280.5 g 3-bromoanisole in 300 ml analytical grade tetrahydrofuran were then added dropwise. The reaction mixture was allowed to after-react for 1 hour and was then cooled to 20° C. 290 g 9-dimethyl-aminomethyl-3,3-dimethyl-1,5-dioxa-spiro[5.5]undecan-8-one in 700 ml analytical grade tetrahydrofuran were added dropwise at this temperature. The mixture was allowed to after-react overnight at room temperature. First 200 ml of a 20% ammonium chloride solution, then 300 ml water and then 100 ml of a 32% hydrochloric acid solution were then added dropwise at a temperature of 10–15° C. The phases were separated and the aqueous phase was extracted twice with 400 ml ethyl acetate each time. The organic phase was dried over magnesium sulfate and the solvent was then evaporated in vacuo. 1,000 ml petroleum ether were added to the crude base obtained in this way. The title compound started to crystallize out after a short time. To complete the crystallization, 2,100 ml diisopropyl ether were added and the mixture was subsequently stirred at 5° C. for 2 hours. The solid was filtered off with suction, washed with diisopropyl ether and then dried in vacuo. 156 g (41.2% of theory) were obtained in this way in the form of a white solid.

Stage 4 rac-cis-[4-Dimethylaminomethyl-3-hydroxy-3-(3-methoxy-phenyl)-cyclohexanone]hydrochloride (1) and 4-dimethylaminomethyl-3-(3-methoxy-phenyl)-cyclohex-2-enone hydrochloride (6)

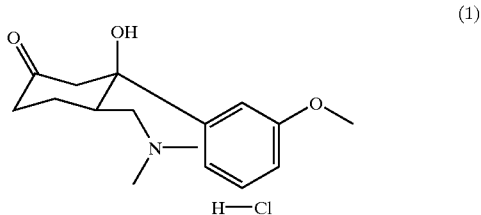

(1)

a) 4-Dimethylaminomethyl-3-(3-methoxy-phenyl)-cyclohex-2-enone hydrochloride (compound 6)

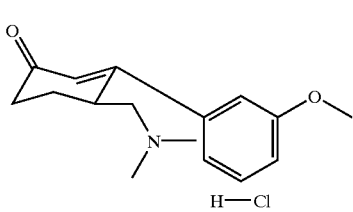
(6)

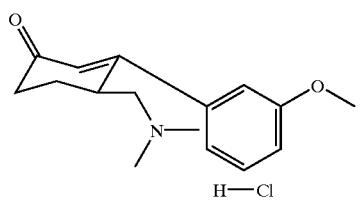

182 g 9-dimethylaminomethyl-8-(3-methoxy-phenyl)-3,3-dimethyl-1,5-dioxa-spiro[5.5]undecan-8-ol were dissolved in 1,200 ml tetrahydrofuran and the reaction mixture was cooled to 5° C. A mixture of 600 ml 32% hydrochloric acid solution and 600 ml water was added at this temperature. The mixture was stirred at room temperature for 72 hours. When the reaction had ended 500 ml ethyl acetate were added at 5° C. and the reaction mixture was then brought to pH 12 with 32% sodium hydroxide solution. The phases were separated and the aqueous phase was washed three times with 300 ml ethyl acetate each time. The combined organic phases were then washed twice with 100 ml saturated sodium chloride solution each time, dried over magnesium sulfate and then freed from the solvent. Purification was carried out via hydrochloride formation. For this, 4-dimethylaminomethyl-3-(3-methoxy-phenyl)-cyclohex-2-enone base was dissolved in 500 ml acetone and an equimolar amount of water and trimethylchlorosilane was added. The hydrochloride which had precipitated out was filtered off with suction and dried in vacuo. 63.6 g (78.9% of theory) 4-dimethylaminomethyl-3-(3-methoxy-phenyl)-cyclohex-2-enone hydrochloride were obtained in this way.

b) rac-cis-[4-Dimethylaminomethyl-3-hydroxy-3-(3-methoxy-phenyl)-cyclohexanone]hydrochloride (compound 1)

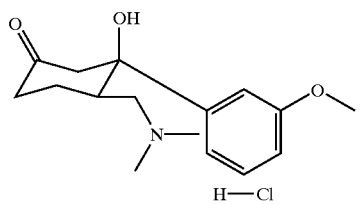

150 g 9-dimethylaminomethyl-8-(3-methoxy-phenyl)-3,3-dimethyl-1,5-dioxa-spiro[5.5]undecan-8-ol were dissolved in tetrahydrofuran and the solution was cooled to −10° C. 1,000 ml of a mixture of water and 32% hydrochloric acid (5:1) were then added dropwise. The mixture was left overnight at 5° C. 750 ml diethyl ether were then added and the pH was then brought to 12 with 200 ml 32% sodium hydroxide solution. The phases were separated and the aqueous phase was extracted twice with 200 ml diethyl ether each time. The combined organic phases were washed with 200 ml saturated sodium chloride solution and dried over sodium sulfate and the solvent was then evaporated in vacuo. rac-cis-[4-Dimethylaminomethyl-3-hydroxy-3-(3-methoxy-phenyl)-cyclohexanone base was dissolved in acetone, and an equimolar amount of water and trimethylchlorosilane was added. The hydrochloride which had precipitated out was filtered off with suction and dried in vacuo. 67 g (59% of theory) rac-cis-[4-dimethylaminomethyl-3-hydroxy-3-(3-methoxy-phenyl)-cyclohexanone] hydrochloride were obtained in this way.

Example 2 rac-cis-[4-Dimethylaminomethyl-3-(3-methoxy-phenyl)-cyclohexanone]hydrochloride (compound 2) and rac-trans-[4-dimethylaminomethyl-3-(3-methoxy-phenyl)-cyclohexanone]hydrochloride (compound 3)

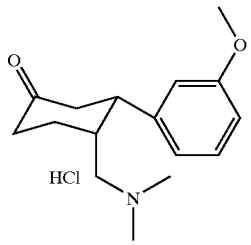
(2)

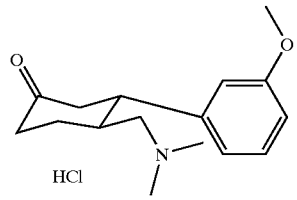
(3)

28.5 g 4-dimethylaminomethyl-3-(3-methoxy-phenyl)-cyclohex-2-enone, which was prepared according to example 1 stage 4a), were dissolved in 250 ml absolute methanol. 2.8 g palladium-on-charcoal (10%) were added as a catalyst, while stirring and passing dry nitrogen over. Hydrogenation was then carried out for five hours under a pressure of 0.2 bar and at a temperature of 20° C. After filtration, the solvent was evaporated off in vacuo and the residue was purified by column chromatography on silica gel with ethyl acetate/methanol/diisopropyl ether=4/1/5 as the eluting agent. 7.5 g rac-cis-[4-dimethylaminomethyl-3-(3-methoxy-phenyl)]-cyclohexanone in the form of an oil were obtained as the first product fraction. To prepare the hydrochloride, the base was dissolved in acetone, and an equimolar amount of water and trimethylchlorosilane was added. The hydrochloride which had precipitated out was filtered off with suction and dried in vacuo. 7.2 g (25.4% of theory) rac-cis-[4-dimethylaminomethyl-3-(3-methoxy-phenyl)]-cyclohexanone hydrochloride were obtained in this way. The second product fraction gave 7.8 g rac-trans-[4-dimethylaminomethyl-3-(3-methoxy-phenyl)]-cyclohexanone, likewise as an oil. To prepare the hydrochloride, the base was dissolved in acetone, and an equimolar amount of water and trimethylchlorosilane was added. The hydrochloride which had precipitated out was filtered off with suction and dried in vacuo. 7.4 g (26.1% of theory) rac-trans-[4-dimethylaminomethyl-3-(3-methoxy-phenyl)]-cyclohexanone hydrochloride were obtained in this way.

Example 3 rac-cis-[4-Dimethylaminomethyl-3-(3-hydroxy-phenyl)-cyclohexanone (compound 4) and rac-trans-[4-dimethylaminomethyl-3-(3-hydroxy-phenyl)-cyclohexanone (compound 5)

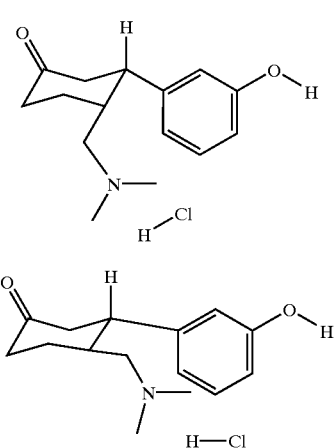

Stage 1

8-[3-(tert-Butyl-diphenyl-silanyloxy)-phenyl]-9-dimethylaminomethyl-3,3-dimethyl-1,5-dioxa-spiro[5.5]undecan-8-ol

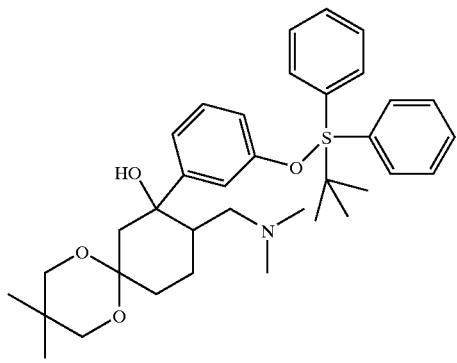

17.3 g magnesium filings were initially introduced into tetrahydrofuran. 293 g (3-bromo-phenoxy)-tert-butyl-diphenylsilane in 150 ml tetrahydrofuran were then added dropwise (under gentle reflux). The mixture was allowed to after-react for 1 hour. 142 g 9-dimethylaminomethyl-1,5-dioxa-spiro[5.5]undecan-8-one, which was prepared according to example 1, stage 2, were then added dropwise at 20° C. The mixture was stirred at room temperature for 10 hours. Hydrolysis was then carried out at 10–15° C. with 200 ml 20% ammonium chloride solution and then with 500 ml water. The aqueous phase was extracted twice with 300 ml ethyl acetate each time. The combined organic phases were dried over magnesium sulfate and the solvent was then evaporated in vacuo. The residue was purified on silica gel with ethyl acetate/methanol=9/1. 197 g (60% of theory) of the title compound were obtained in this way.

Stage 2

3-[3-(tert-Butyl-diphenyl-silanyloxy)-phenyl]-4-dimethylaminomethyl-cyclohex-2-enone 197 g 8-[3-(tert-Butyl-diphenyl-silanyloxy)-phenyl]-9-dimethylaminomethyl-3,3-dimethyl-1,5-dioxa-spiro[5.5]undecan-8-ol were dissolved in tetrahydrofuran and the solution was cooled to 5° C. A mixture of 300 ml concentrated hydrochloric acid and 300 ml water was added dropwise at this temperature. The mixture was then stirred at room temperature for 10 hours. 400 ml ethyl acetate were then added, while cooling with ice, and the pH was then brought to 12 with 32% sodium hydroxide solution. The phases were separated and the aqueous phase was extracted three times with 400 ml ethyl acetate each time. The combined organic phases were washed twice with 100 ml saturated sodium chloride solution each time and dried over magnesium sulfate and the solvent was then evaporated in vacuo. The residue was purified on silica gel with ethyl acetate/methanol=1/1. 68 g (42% of theory) of the title compound were obtained in this way.

Stage 3 rac-cis-[4-Dimethylaminomethyl-3-(3-hydroxy-phenyl)-cyclohexanone (4) and rac-trans-[4-dimethylaminomethyl-3-(3-hydroxy-phenyl)-cyclohexanone (5)

25 g 3-[3-(tert-butyl-diphenyl-silanyloxy)-phenyl]-4-dimethylaminomethyl-cyclohex-2-enone were dissolved in 110 ml absolute methanol. 2,8 g palladium-on-charcoal (10%) were added as a catalyst, while stirring and passing dry nitrogen over. Hydrogenation was then carried out for five hours under a pressure of 0.2 bar and at a temperature of 20° C. After filtration the solvent was evaporated off in vacuo and the residue was dissolved in 60 ml tetrahydrofuran. 15 ml tetrabutylammonium fluoride were then added at room temperature. When the reaction had ended the mixture was quenched with water and then extracted with ethyl acetate. The organic phase was washed with saturated sodium chloride solution. The organic phase was then dried over magnesium sulfate and the solvent was evaporated in vacuo. The residue was purified by column chromatography on silica gel with ethyl acetate/methanol/diisopropyl ether= 4/1/5 as the eluting agent. 5 g rac-cis-[4-dimethylaminomethyl-3-(3-hydroxy-phenyl)-cyclohexanone in the form of an oil were obtained as the first product fraction. To prepare the hydrochloride, the base was dissolved in acetone, and an equimolar amount of water and trimethylchlorosilane was added. The hydrochloride which had precipitated out was filtered off with suction and dried in vacuo. 4.8 g (32.9% of theory) rac-cis-[4-dimethylaminomethyl-3-(3-hydroxy-phenyl)-cyclohexanone hydrochloride were obtained in this way. The second product fraction gave 3.5 g rac-trans-[4-dimethylaminomethyl-3-(3-hydroxy-phenyl)-cyclohexanone, likewise as an oil. To prepare the hydrochloride, the base was dissolved in acetone, and an equimolar amount of water and trimethylchlorosilane was added. The hydrochloride which had precipitated out was filtered off with suction and dried in vacuo. 3.2 g (21.9% of theory) rac-trans-[4-dimethylaminomethyl-3-(3-hydroxy-phenyl)-cyclohexanone hydrochloride were obtained in this way.

Example 4

The following examples were synthesized according to the instructions given and the structures are confirmed by NMR analyses.

4-dimethylaminomethyl-3-phenyl-cyclohex-2-enone;
4-dimethylaminomethyl-3-(3-hydroxy-phenyl)-cyclohex-2-enone;
rac-trans-4-dimethylaminomethyl-3-phenyl-cyclohexanone;
rac-cis-4-dimethylaminomethyl-3-phenyl-cyclohexanone;
4-dimethylaminomethyl-3-(4-methoxy-phenyl)-cyclohex-2-enone;
4-dimethylaminomethyl-3-naphthalen-2-yl-cyclohex-2-enone;
rac-trans-4-dimethylaminomethyl-3-hydroxy-3-naphthalen-2-yl-cyclohexanone;
rac-trans-4-dimethylaminomethyl-3-(3-fluoro-phenyl)-cyclohexanone;
rac-cis-4-dimethylaminomethyl-3-(3-fluoro-phenyl)-cyclohexanone;
rac-cis-4-dimethylaminomethyl-3-hydroxy-3-(2-methoxy-phenyl)-cyclohexanone;
rac-cis-4-dimethylaminomethyl-3-hydroxy-3-(6-methoxy-naphthalen-2-yl)-cyclohexanone;
4-dimethylaminomethyl-3-(6-methoxy-naphthalen-2-yl)-cyclohex-2-enone;
rac-cis-3-biphenyl-4-yl-4-dimethylaminomethyl-3-hydroxy-cyclohexanone;
3-(3-difluoromethyl-phenyl)-4-dimethylaminomethyl-cyclohex-2-enone;
4-dimethylaminomethyl-3-(3-fluoro-phenyl)-cyclohex-2-enone;
3-(3,4-difluoro-phenyl)-4-dimethylaminomethyl-cyclohex-2-enone;
4-dimethylaminomethyl-3-(4-fluoro-phenyl)-cyclohex-2-enone;
4-dimethylaminomethyl-3-(4-trifluoromethyl-phenyl)-cyclohex-2-enone;
3-(3,5-dichloro-phenyl)-4-dimethylaminomethyl-cyclohex-2-enone;
3-(3,5-difluoro-phenyl)-4-dimethylaminomethyl-cyclohex-2-enone; and
rac-cis-3-(3,5-difluoro-phenyl)-4-dimethylaminomethyl-3-hydroxy-cyclohexanone Example 5

Pharmacological Studies

Writhing Test

The antinociceptive activity of the compounds according to the invention was investigated in mice in a phenylquinone-induced writhing test, as modified by I. C. Hendershot, J. Forsaith, J. Pharmacol. Exp. Ther. 125, 237–240 (1959). Male NMRI mice weighing 25–30 g were used. Groups of 10 animals per substance dose received 0.3 ml/mouse of a 0.02% aqueous solution of phenylquinone (phenylbenzoquinone, Sigma, Deisenhofen; preparation of the solution with the addition of 5% ethanol and storage in a water bath at 45° C.) administered intraperitoneally 10 minutes after intravenous administration of a compound according to the invention. The animals were placed individually in observation cages. The number of pain-induced stretching movements (so-called writhing reactions, i.e. straightening of the body with stretching of the hind extremities) was counted by means of a push-button counter for 5–20 minutes after the administration of phenylquinone. Animals which received physiological saline solution i.v. and phenylquinone i.v. were also used as a control.

All substances were tested in a standard dose of 10 mg/kg. The percentage inhibition (% inhibition) of the writhing reactions by a substance was calculated according to the following equation:

$$\% \text{ inhibition} = 100 - [WR \text{ treated animals}/WR \text{ control} \times 100]$$

All compounds according to the invention investigated showed a moderate to potent analgesic action.

The results of selected writhing investigations are summarized in Table 1.

TABLE 1

Analgesia Effect in Mouse Writhing test

| Compound | % inhibition of the writhing reactions 10 mg/kg i.v. |
|---|---|
| 2 | 96 |
| 3 | 92 |
| 4 | 100 |

We claim:
1. An aminomethyl-phenyl-cyclohexanone derivative of formula I or Ia,

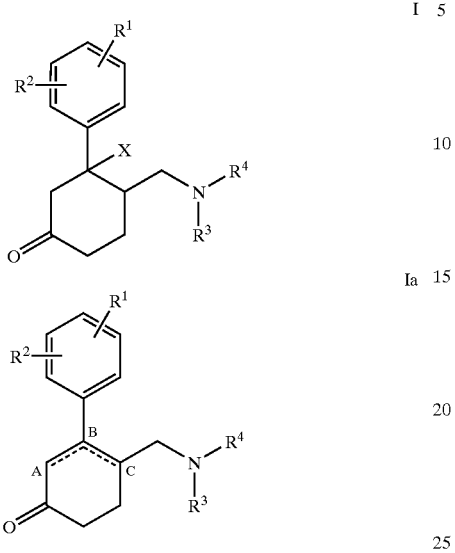

wherein
R$^1$ and R$^2$ independently of one another are R$^5$ or YR$^5$,
  wherein Y is C$_1$–C$_{10}$-alkyl, C$_2$–C$_{10}$-alkenyl or C$_2$–C$_{10}$ alkinyl, branched or unbranched and mono- or polysubstituted or unsubstituted,
  wherein R$^5$ is H; F; Cl; Br; I; CN; NO$_2$; C$_1$–C$_8$-alkyl, C$_2$–C$_8$-alkenyl or C$_2$–C$_8$-alkinyl, in each case branched or unbranched and mono- or polysubstituted or unsubstituted; C$_3$–C$_7$-cycloalkyl, saturated or unsaturated and mono- or polysubstituted or unsubstituted, or a corresponding heterocyclic radical, in which one carbon atom in the ring is replaced by an S, O or NR$^6$, wherein R$^6$ is
    H; or C$_1$–C$_{10}$-alkyl, C$_2$–C$_{10}$-alkenyl or C$_2$–C$_{10}$-alkinyl, in each case branched or unbranched and mono- or polysubstituted or unsubstituted;
  aryl or heteroaryl, in each case mono- or polysubstituted or unsubstituted;
  OR$^7$, OC(O)R$^7$, OC(O)OR$^7$, OC(S)R$^7$, C(O)R$^7$, C(O)OR$^7$, C(S)R$^7$, C(S)OR$^7$, SR$^7$, S(O)R$^7$ or S(O$_2$)R$^7$, wherein R$^7$ is
    H; C$_1$–C$_{18}$-alkyl, C$_2$–C$_{18}$-alkenyl or C$_2$–C$_{18}$-alkinyl, in each case branched or unbranched and mono- or polysubstituted or unsubstituted; C$_3$–C$_7$-cycloalkyl, saturated or unsaturated and mono- or polysubstituted or unsubstituted, or a corresponding heterocyclic radical, in which one carbon atom in the ring is replaced by an S, O or NR$^8$, where R$^8$ is
      H; or C$_1$–C$_{10}$-alkyl, C$_2$–C$_{10}$-alkenyl or C$_2$–C$_{10}$-alkinyl, in each case branched or unbranched and mono- or polysubstituted or unsubstituted;
    or alkylaryl, saturated or unsaturated and mono- or polysubstituted or unsubstituted; or aryl or heteroaryl, in each case mono- or polysubstituted or unsubstituted; or
  NR$^9$R$^{10}$, C(O)NR$^9$R$^{10}$ or S(O$_2$)NR$^9$R$^{10}$, wherein R$^9$ and R$^{10}$ independently of one another are
    H; C$_1$–C$_{18}$-alkyl, C$_2$–C$_{18}$-alkenyl or C$_2$–C$_{18}$-alkinyl, in each case branched or unbranched and mono- or polysubstituted or unsubstituted; C$_3$–C$_7$- cycloalkyl, saturated or unsaturated and mono- or polysubstituted or unsubstituted, or a corresponding heterocyclic radical, in which one carbon atom in the ring is replaced by S, O or NR$^{11}$, wherein R$^{11}$ is
      H; or C$_1$–C$_{10}$-alkyl, C$_2$–C$_{10}$-alkenyl or C$_2$–C$_{10}$-alkinyl, in each case branched or unbranched and mono- or polysubstituted or unsubstituted;
    or alkylaryl, saturated or unsaturated and mono- or polysubstituted or unsubstituted; aryl or heteroaryl, in each case mono- or polysubstituted or unsubstituted; or
  R$^9$ and R$^{10}$ together form a C$_3$–C$_7$-cycloalkyl, saturated or unsaturated and mono- or polysubstituted or unsubstituted, or a corresponding heterocyclic radical, in which one carbon atom in the ring is replaced by an S, O or NR$^{12}$, where R$^{12}$ is chosen from
    H; or C$_1$–C$_{10}$-alkyl, C$_2$–C$_{10}$-alkenyl or C$_2$–C$_{10}$-alkinyl, in each case branched or unbranched and mono- or polysubstituted or unsubstituted; or
R$^1$ and R$^2$ together form —CH=CH—CH=CH—, resulting in a naphthyl system which is mono- or polysubstituted,
X is H; F; Cl; Br; I; CF$_3$; O—S(O$_2$)—C$_6$H$_4$-pCH$_3$; OR$^{13}$ or OC(O)R$^{13}$, wherein R$^{13}$ is
  H; C$_1$–C$_{10}$-alkyl, C$_2$–C$_{10}$-alkenyl or C$_2$–C$_{10}$-alkinyl, in each case branched or unbranched and mono- or polysubstituted or unsubstituted; C$_3$–C$_7$-cycloalkyl, saturated or unsaturated and mono- or polysubstituted or unsubstituted, or a corresponding heterocyclic radical, in which one carbon atom in the ring is replaced by an N, S or O; alkylaryl, saturated or unsaturated and mono- or polysubstituted or unsubstituted; or aryl or heteroaryl, in each case mono- or polysubstituted or unsubstituted; o or
if according to formula Ia the compound contains no X, a double bond is formed between carbon atoms "A" and "B", or carbon atoms "B" and "C"; and
R$^3$, R$^4$ independently of one another are
H; C$_1$–C$_{10}$-alkyl, C$_2$–C$_{10}$-alkenyl or C$_2$–C$_{10}$-alkinyl, in each case branched or unbranched and mono- or polysubstituted or unsubstituted; C$_3$–C$_7$-cycloalkyl, saturated or unsaturated and mono- or polysubstituted or unsubstituted, or a corresponding heterocyclic radical, in which one carbon atom in the ring is replaced by an N, S or O; alkylaryl, saturated or unsaturated and mono- or polysubstituted or unsubstituted; or aryl or heteroaryl, in each case mono- or polysubstituted or unsubstituted; or
R$^3$ and R$^4$ together form a C$_3$–C$_7$-cycloalkyl, saturated or unsaturated and mono- or polysubstituted or unsubstituted, or a corresponding heterocyclic radical, in which one carbon atom in the ring is replaced by an S, O or NR$^{14}$, wherein R$^{14}$ is
  H; or C$_1$–C$_{10}$-alkyl, C$_2$–C$_{10}$-alkenyl or C$_2$–C$_{10}$-alkinyl, in each case branched or unbranched and mono- or polysubstituted or unsubstituted,
its diastereomers, enantiomers and salts formed with a physiologically tolerated acid,
with the proviso that
  if X=OH, R$^2$=H, R$^3$ and R$^4$ are each CH$_3$, then R$^1$ is not R$^5$, wherein R$^5$ is
    (1) OR$^7$, where R$^7$ is H, CH$_3$ or an unsubstituted or substituted pyridyl, thienyl, thiazoyl or phenyl group;

(2) OC(O)OR$^7$, where R$^7$ is C$_1$–C$_5$-alkyl, or (3) OC(O)R$^7$, where R$^7$ is C$_{1-5}$-alkyl, NH—C$_6$H$_4$—C$_{1-3}$-alkyl, C$_6$H$_4$—OC(O)C$_{1-3}$-alkyl, C$_6$H$_4$—CH$_2$—N(C$_{1-4}$-alkyl)$_2$, C$_6$H$_4$—CH$_2$—(N-4-morpholino) or CHZ'-NHZ", where Z' and Z" are identical or different and are H or C$_{1-6}$-alkyl, or that if X=H, or according to formula Ia a double bond is formed between carbon atoms "A" and "B", R$^2$=H, either or both of R$^3$ and R$^4$ are C$_{1-6}$-alkyl, aryl or C$_{3-7}$-cycloalkyl, then R$^1$ is not H, C$_{1-6}$-alkoxy, O—C$_{3-7}$-cycloalkyl, O-aryl or O-heterocyclyl.

2. A hydrochloride salt of an aminomethyl-phenyl-cyclohexanone derivative according to claim 1.

3. An aminomethyl-phenyl-cyclohexanone derivative according to claim 1, wherein R$^1$ is R$^5$, wherein R$^5$ is H; F; Cl; Br; I; CHF$_2$; CF$_3$; NO$_2$; NH$_2$; C$_1$–C$_4$-alkyl or C$_2$–C$_4$-alkenyl, branched or unbranched and mono- or polysubstituted or unsubstituted; aryl, substituted or unsubstituted; OR$^7$, C(O)OR$^7$ or SR$^7$, wherein R$^7$ is H; or C$_1$–C$_4$-alkyl, branched or unbranched and mono- or polysubstituted or unsubstituted;

or S(O$_2$)NR$^9$R$^{10}$, wherein R$^9$ and R$^{10}$ independently of one another are H; or C$_1$–C$_4$-alkyl, branched or unbranched and mono- or polysubstituted or unsubstituted.

4. An aminomethyl-phenyl-cyclohexanone derivative according to claim 3, wherein R$^1$ is R$^5$ and R$^5$ is OR$^7$, C(O)OR$^7$ or SR$^7$, wherein R$^7$ is H, CF$_3$ or CH$_3$.

5. An aminomethyl-phenyl-cyclohexanone derivative according to claim 3, wherein R$^1$ is R$^5$, and R$^5$ is H, F, Cl, OH, CH$_3$, C$_2$H$_5$, C$_2$H$_3$, CHF$_2$, CF$_3$, SCH$_3$, OCF$_3$, OCH$_3$, OC$_2$H$_5$, C(O)OCH$_3$, C(O)OC$_2$H$_5$ or phenyl.

6. An aminomethyl-phenyl-cyclohexanone derivative according to claim 1, wherein R$^2$=R$^5$, and R$^5$ is H; F; Cl; Br; I; SCH$_3$; C$_1$–C$_4$-alkyl, C$_2$–C$_4$-alkenyl, branched or unbranched and mono- or polysubstituted or unsubstituted; or OR$^7$, wherein R$^7$ is branched or unbranched and mono- or polysubstituted or unsubstituted C$_1$–C$_4$-alkyl.

7. An aminomethyl-phenyl-cyclohexanone derivative according to claim 6, wherein R$^2$=R$^5$, and R$^5$ is CF$_3$.

8. An aminomethyl-phenyl-cyclohexanone derivative according to claim 6, wherein R$^2$=R$^5$, and R$^5$ is OCH$_3$.

9. An aminomethyl-phenyl-cyclohexanone derivative according to claim 1, wherein R$^1$ is different from R$^2$.

10. An aminomethyl-phenyl-cyclohexanone derivative according to claim 1, wherein R$^1$ and R$^2$ together form —CH=CH—CH=CH—, resulting in naphthyl system which is unsubstituted, mono- or polysubstituted.

11. An aminomethyl-phenyl-cyclohexanone derivative according to claim 10, wherein the naphthyl system formed by R$^1$ and R$^2$ is substituted by halogen, OC$_{1-3}$-alkyl or C$_{1-3}$-alkyl.

12. An aminomethyl-phenyl-cyclohexanone derivative according to claim 11, wherein the naphthyl system formed by R$^1$ and R$^2$ is substituted by OCH$_3$.

13. An aminomethyl-phenyl-cyclohexanone derivative according to claim 1, wherein X is H; F; Cl; OH; CF$_3$; O—S(O$_2$)—C$_6$H$_4$-pCH$_3$ or OC(O)R$^7$, wherein R$^7$ is H or branched or unbranched and mono- or polysubstituted or unsubstituted C$_1$–C$_4$-alkyl or C$_2$–C$_4$-alkenyl, or if according to formula Ia the compound contains no X, a double bond is formed between carbon atoms "A" and "B" or carbon atoms "B" and "C".

14. An aminomethyl-phenyl-cyclohexanone derivative according to claim 13, wherein X is H; F; Cl; OH; O—S(O$_2$)—C$_6$H$_4$-pCH$_3$; or OC(O)R$^7$, wherein R$^7$=C$_1$–C$_4$-alkyl.

15. An aminomethyl-phenyl-cyclohexanone derivative according to claim 14, wherein X is OC(O)CH$_3$.

16. An aminomethyl-phenyl-cyclohexanone derivative according to claim 14, wherein X is H or OH.

17. An aminomethyl-phenyl-cyclohexanone derivative according to claim 1, wherein R$^3$ and R$^4$ independently of one another are branched or unbranched and mono- or polysubstituted or unsubstituted C$_1$–C$_4$-alkyl, or R$^3$ and R$^4$ together form a saturated or unsaturated and mono- or polysubstituted or unsubstituted C$_3$–C$_7$-cycloalkyl.

18. An aminomethyl-phenyl-cyclohexanone derivative according to claim 17, wherein R$^3$ and R$^4$ independently of one another are CH$_3$.

19. An aminomethyl-phenyl-cyclohexanone derivative according to claim 1, selected from the group consisting of:

rac-cis-[4-dimethylaminomethyl-3-hydroxy-3-(3-methoxy-phenyl)-cyclohexanone];

rac-cis-[4-dimethylaminomethyl-3-(3-methoxy-phenyl)-cyclohexanone];

rac-trans-[4-dimethylaminomethyl-3-(3-methoxy-phenyl)-cyclohexanone];

rac-cis-[4-dimethylaminomethyl-3-(3-hydroxy-phenyl)-cyclohexanone];

rac-trans-[4-dimethylaminomethyl-3-(3-hydroxy-phenyl)-cyclohexanone];

4-dimethylaminomethyl-3-(3-methoxy-phenyl)-cyclohex-2-enone;

4-dimethylaminomethyl-3-phenyl-cyclohex-2-enone;

4-dimethylaminomethyl-3-(3-hydroxy-phenyl)-cyclohex-2-enone;

rac-trans-4-dimethylaminomethyl-3-phenyl-cyclohexanone;

rac-cis-4-dimethylaminomethyl-3-phenyl-cyclohexanone;

4-dimethylaminomethyl-3-(4-methoxy-phenyl)-cyclohex-2-enone;

4-dimethylaminomethyl-3-naphthalen-2-yl-cyclohex-2-enone;

rac-trans-4-dimethylaminomethyl-3-hydroxy-3-naphthalen-2-yl-cyclohexanone;

rac-trans-4-dimethylaminomethyl-3-(3-fluoro-phenyl)-cyclohexanone;

rac-cis-4-dimethylaminomethyl-3-(3-fluoro-phenyl)-cyclohexanone;

rac-cis-4-dimethylaminomethyl-3-hydroxy-3-(2-methoxy-phenyl)-cyclohexanone;

rac-cis-4-dimethylaminomethyl-3-hydroxy-3-(6-methoxy-naphthalen-2-yl)-cyclohexanone;

4-dimethylaminomethyl-3-(6-methoxy-naphthalen-2-yl)-cyclohex-2-enone;

rac-cis-3-biphenyl-4-yl-4-dimethylaminomethyl-3-hydroxy-cyclohexanone;

3-(3-difluoromethyl-phenyl)-4-dimethylaminomethyl-cyclohex-2-enone;

4-dimethylaminomethyl-3-(3-fluoro-phenyl)-cyclohex-2-enone;

3-(3,4-difluoro-phenyl)-4-dimethylaminomethyl-cyclohex-2-enone;

4-dimethylaminomethyl-3-(4-fluoro-phenyl)-cyclohex-2-enone;

4-dimethylaminomethyl-3-(4-trifluoromethyl-phenyl)-cyclohex-2-enone;

3-(3,5-dichloro-phenyl)-4-dimethylaminomethyl-cyclohex-2-enone;

3-(3,5-difluoro-phenyl)-4-dimethylaminomethyl-cyclohex-2-enone; and rac-cis-3-(3,5-difluoro-phenyl)-4-dimethylaminomethyl-3-hydroxy-cyclohexanone.

20. A process for preparing an aminomethyl-phenyl-cyclohexanone derivative according to claim 1, wherein the derivative is of formula Ia, the process comprising reacting a compound of formula II

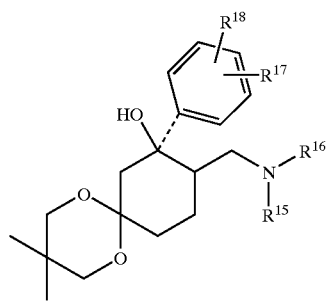

II wherein $R^{15}=R^3$, $R^{16}=R^4$, $R^{17}=R^1$ and $R^{18}=R^2$, with an acid at room temperature to obtain a compound of formula Ia or a compound of formula I wherein X=H.

21. A process according to claim 20, wherein the acid is hydrochloric acid, formic acid or acetic acid.

22. A process according to claim 21, further comprising purifying the compound of formula Ia.

23. A process for preparing an aminomethyl-phenyl-cyclohexanone derivative according to claim 1, wherein the derivative is of formula I wherein X=H, the process comprising hydrogenating a compound of formula Ia with catalytically activated hydrogen.

24. A process according to claim 23, wherein the activated hydrogen is catalytically activated with platinum or palladium as a catalyst absorbed on a support material.

25. A process according to claim 24, wherein the activated hydrogen is catalytically activated with platinum or palladium as a catalyst absorbed on active charcoal.

26. A process according to claim 23, wherein the compound of formula Ia is hydrogenated in ethyl acetate or a $C_1$–$C_4$-alkyl alcohol and under a pressure of 0.1 to 10 bar.

27. A process according to claim 23, wherein the compound of formula Ia is hydrogenated at a temperature of between 20° C. to 80° C.

28. A process according to claim 23, further comprising purifying the compound of formula I where X=H.

29. A process according to claim 23, wherein the catalytically activated hydrogen is activated with platinum or palladium as a catalyst absorbed on active charcoal, and wherein the compound of formula Ia is hydrogenated in ethyl acetate or a $C_1$–$C_4$-alkyl alcohol under a pressure of 0.1 to 10 bar, and at a temperature of between 20° C. to 80° C.

30. A process for preparing an aminomethyl-phenyl-cyclohexanone derivative according to claim 1, wherein the derivative is of formula I wherein X=OH, the process comprising reacting a compound of formula II

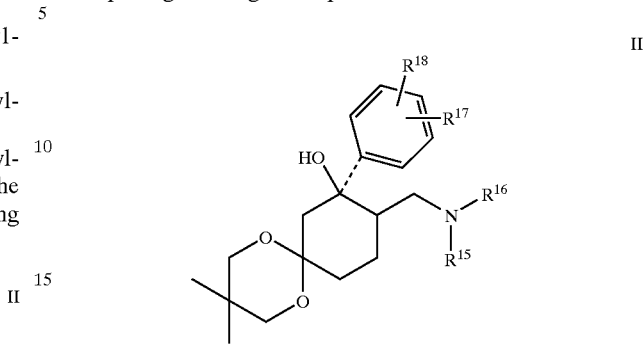

II wherein $R^{15}=R^3$, $R^{16}=R^4$, $R^{17}=R^1$ and $R^{18}=R^2$, with an acid at a temperature of between 0° C. and 5° C., to form a derivative of formula I wherein X=OH.

31. A process according to claim 30, wherein the acid is hydrochloric acid.

32. A process according to claim 30, further comprising purifying the derivative of formula I wherein X=OH.

33. A process for preparing an aminomethyl-phenyl-cyclohexanone derivative according to claim 1, wherein the derivative is of formula I wherein X is F, Cl, Br, I or $CF_3$, the process comprising substituting the X=OH group of formula I with F, Cl, Br, I or $CF_3$ to form a derivative of formula I wherein X is F, Cl, Br, I or $CF_3$.

34. A process according to claim 33, further comprising purifying the derivative of formula I wherein X is F, Cl, Br, I or $CF_3$.

35. A process for preparing an aminomethyl-phenyl-cyclohexanone derivative according to claim 1, wherein the derivative is of formula I wherein X is $OR^{13}$, the process comprising etherifying the X=OH group of formula I with a halide of the formula III

III wherein $R^{19}=R^{13}$, to form a derivative of formula I wherein X is $OR^{13}$.

36. A process according to claim 35, further comprising purifying the derivative of formula I wherein X is $OR^{13}$.

37. A process for preparing an aminomethyl-phenyl-cyclohexanone derivative according to claim 1, wherein the derivative is of formula I wherein X is O—S($O_2$)—$C_6H_4$—$CH_3$ or $OC(O)R^{13}$, the process comprising esterifying the X=OH group of formula I with Cl—S($O_2$)—$C_6H_4$—$CH_3$ to form a derivative of formula I wherein X is O—S($O_2$)—$C_6H_4$—$CH_3$, or with an acid chloride of the formula IV

IV wherein $R^{20}=R^{13}$ to form a derivative of formula I wherein X is $OC(O)R^{13}$.

38. A process according to claim 37, further comprising purifying the derivative of formula I wherein X is $OC(O)R^{13}$.

39. A process according to claim 20, wherein the compound of formula II is prepared by
(1) reacting 3,3-dimethyl-1,5-dioxa-spiro[5.5]-undecan-8-one

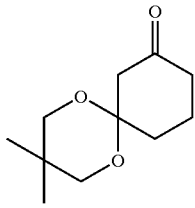

with an immonium salts of formula V or with formaldehyde and an amine of the formula VI, wherein $R^{15}=R^3$ and $R^{16}=R^4$

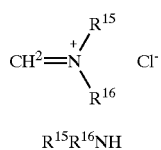   V $R^{15}R^{16}NH$   VI to form a Mannich base; and
(2) reacting the Mannich base with an organometallic compound of the formula VII,

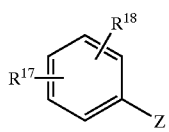   VII in which Z denotes MgCl, MgBr, MgI or lithium and $R^{17}=R^1$ and $R^{18}=R^2$, at a temperature of between −70° C. and 60° C.

40. A process according to claim 39, wherein the reaction in step 2 is in solvent comprising at least one of diethyl ether and tetrahydrofuran.

41. A process according to claim 20, wherein the aminomethyl-phenyl-cyclohexanone derivative of formula Ia comprises at least one $C(O)OCH_3$, $OC(O)OCH_3$ or $C(S)OCH_3$, the process further comprising hydrolyzing at least one of the at least one $C(O)OCH_3$, $OC(O)OCH_3$ or $C(S)OCH_3$ with KOH solution or NaOH solution in methanol at 40° C.–60° C. to obtain a hydrolyzed product, and purifying the hydrolyzed product.

42. A process according to claim 23, wherein the aminomethyl-phenyl-cyclohexanone derivative of formula I wherein X=H comprises at least one $C(O)OCH_3$, $OC(O)OCH_3$ or $C(S)OCH_3$, the process further comprising hydrolyzing at least one of the at least one $C(O)OCH_3$, $OC(O)OCH_3$ or $C(S)OCH_3$ with KOH solution or NaOH solution in methanol at 40° C.–60° C. to obtain a hydrolyzed product, and purifying the hydrolyzed product.

43. A process according to claim 30, wherein the aminomethyl-phenyl-cyclohexanone derivative of formula I wherein X=OH comprises at least one $C(O)OCH_3$, $OC(O)OCH_3$ or $C(S)OCH_3$, the process further comprising hydrolyzing at least one of the at least one $C(O)OCH_3$, $OC(O)OCH_3$ or $C(S)OCH_3$ with KOH solution or NaOH solution in methanol at 40° C.–60° C. to obtain a hydrolyzed product, and purifying the hydrolyzed product.

44. A process according to claim 33, wherein the aminomethyl-phenyl-cyclohexanone derivative of formula I wherein X is F, Cl, Br, I or $CF^3$ comprises at least one $C(O)OCH_3$, $OC(O)OCH_3$ or $C(S)OCH_3$, the process further comprising hydrolyzing at least one of the at least one $C(O)OCH_3$, $OC(O)OCH_3$ or $C(S)OCH_3$ with KOH solution or NaOH solution in methanol at 40° C.–60° C. to obtain a hydrolyzed product, and purifying the hydrolyzed product.

45. A process according to claim 35, wherein the aminomethyl-phenyl-cyclohexanone derivative of formula I wherein X is $OR^{13}$ comprises at least one $C(O)OCH_3$, $OC(O)OCH_3$ or $C(S)OCH_3$, the process further comprising hydrolyzing at least one of the at least one $C(O)OCH_3$, $OC(O)OCH_3$ or $C(S)OCH_3$ with KOH solution or NaOH solution in methanol at 40° C.–60° C. to obtain a hydrolyzed product, and purifying the hydrolyzed product.

46. A process according to claim 20, wherein in $R^{15}$ to $R^{18}$ according to formula II there is at least one OH group, the method further comprising replacing at least one of the OH group with an $OSi(Ph)_2$tert-but group prior to reacting the compound of formula II with the acid, and removing the $OSi(Ph)_2$tert-but group after the reaction with the acid with tetrabutylammonium fluoride in tetrahydrofuran.

47. A process according to claim 20, wherein in $R^{15}$ to $R^{18}$ according to formula II there is at least one SH group, the method further comprising replacing at least one of the SH group with an S-p-methoxybenzyl group prior to reacting the compound of formula II with the acid, and removing the p-methoxybenzyl group after the reaction with the acid with a metal amine.

48. A process according to claim 47, wherein the metal amine is a sodium amine.

49. A process according to claim 20, wherein in $R^{15}$ to $R^{18}$ according to formula II there is at least one $NH_2$ group, the method further comprising replacing at least one of the $NH_2$ group with an $NO_2$ group prior to reacting the compound of formula II with the acid, and reducing the $NO_2$ to $NH_2$.

50. A process according to claim 23, wherein in $R^{15}$ to $R^{18}$ according to formula II there is at least one OH group, the method further comprising replacing at least one of the OH group with an $OSi(Ph)_2$tert-but group prior to reacting the compound of formula II with the acid, and removing the $OSi(Ph)_2$tert-but group after the reaction with the acid with tetrabutylammonium fluoride in tetrahydrofuran.

51. A process according to claim 23, wherein in $R^{15}$ to $R^{18}$ according to formula II there is at least one SH group, the method further comprising replacing at least one of the SH group with an S-p-methoxybenzyl group prior to reacting the compound of formula II with the acid, and removing the p-methoxybenzyl group after the reaction with the acid with a metal amine.

52. A process according to claim 51, wherein the metal amine is a sodium amine.

53. A process according to claim 23, wherein in $R^{15}$ to $R^{18}$ according to formula II there is at least one $NH_2$ group, the method further comprising replacing at least one of the $NH_2$ group with an $NO_2$ group prior to reacting the compound of formula II with the acid, and reducing the $NO_2$ to $NH_2$.

54. A process according to claim 30, wherein in $R^{15}$ to $R^{18}$ according to formula II there is at least one OH group, the method further comprising replacing at least one of the OH group with an $OSi(Ph)_2$tert-but group prior to reacting the compound of formula II with the acid, and removing the $OSi(Ph)_2$tert-but group after the reaction with the acid with tetrabutylammonium fluoride in tetrahydrofuran.

55. A process according to claim 30, wherein in $R^{15}$ to $R^{18}$ according to formula II there is at least one SH group, the method further comprising replacing at least one of the SH group with an S-p-methoxybenzyl group prior to reacting the compound of formula II with the acid, and removing the p-methoxybenzyl group after the reaction with the acid with a metal amine.

56. A process according to claim 55, wherein the metal amine is a sodium amine.

57. A process according to claim 30, wherein in $R^{15}$ to $R^{18}$ according to formula II there is at least one $NH_2$ group, the method further comprising replacing at least one of the $NH_2$ group with an $NO_2$ group prior to reacting the compound of formula II with the acid, and reducing the $NO_2$ to $NH_2$.

58. A process according to claim 33, wherein in $R^{15}$ to $R^{18}$ according to formula II there is at least one OH group, the method further comprising replacing at least one of the OH group with an $OSi(Ph)_2$tert-but group prior to reacting the compound of formula II with the acid, and removing the $OSi(Ph)_2$tert-but group after the reaction with the acid with tetrabutylammonium fluoride in tetrahydrofuran.

59. A process according to claim 33, wherein in $R^{15}$ to $R^{18}$ according to formula II there is at least one SH group, the method further comprising replacing at least one of the SH group with an S-p-methoxybenzyl group prior to reacting the compound of formula II with the acid, and removing the p-methoxybenzyl group after the reaction with the acid with a metal amine.

60. A process according to claim 59, wherein the metal amine is a sodium amine.

61. A process according to claim 33, wherein in $R^{15}$ to $R^{18}$ according to formula II there is at least one $NH_2$ group, the method further comprising replacing at least one of the $NH_2$ group with an $NO_2$ group prior to reacting the compound of formula II with the acid, and reducing the $NO_2$ to $NH_2$.

62. A process according to claim 35, wherein in $R^{15}$ to $R^{19}$ according to formulae II and III there is at least one OH group, the method further comprising replacing at least one of the OH group with an $OSi(Ph)_2$tert-but group prior to reacting the compound of formula II with the acid, and removing the $OSi(Ph)_2$tert-but group after the reaction with the acid with tetrabutylammonium fluoride in tetrahydrofuran.

63. A process according to claim 35, wherein in $R^{15}$ to $R^{19}$ according to formulae II and III there is at least one SH group, the method further comprising replacing at least one of the SH group with an S-p-methoxybenzyl group prior to reacting the compound of formula II with the acid, and removing the p-methoxybenzyl group after the reaction with the acid with a metal amine.

64. A process according to claim 63, wherein the metal amine is a sodium amine.

65. A process according to claim 35, wherein in $R^{15}$ to $R^{19}$ according to formulae II and III there is at least one $NH_2$ group, the method further comprising replacing at least one of the $NH_2$ group with an $NO_2$ group prior to reacting the compound of formula II with the acid, and reducing the $NO_2$ to $NH_2$.

66. A process according to claim 37, wherein in $R^{15}$ to $R^{18}$ and $R^{20}$ according to formulae II and IV there is at least one OH group, the method further comprising replacing at least one of the OH group with an $OSi(Ph)_2$tert-but group prior to reacting the compound of formula II with the acid, and removing the $OSi(Ph)_2$tert-but group after the reaction with the acid with tetrabutylammonium fluoride in tetrahydrofuran.

67. A process according to claim 37, wherein in $R^{15}$ to $R^{18}$ and $R^{20}$ according to formulae II and IV there is at least one SH group, the method further comprising replacing at least one of the SH group with an S-p-methoxybenzyl group prior to reacting the compound of formula II with the acid, and removing the p-methoxybenzyl group after the reaction with the acid with a metal amine.

68. A process according to claim 67, wherein the metal amine is a sodium amine.

69. A process according to claim 37, wherein in $R^{15}$ to $R^{18}$ and $R^{20}$ according to formulae II and IV there is at least one $NH_2$ group, the method further comprising replacing at least one of the $NH_2$ group with an $NO_2$ group prior to reacting the compound of formula II with the acid, and reducing the $NO_2$ to $NH_2$.

70. A pharmaceutical composition comprising an aminomethyl-phenyl-cyclohexanone derivative of formula I or Ia,

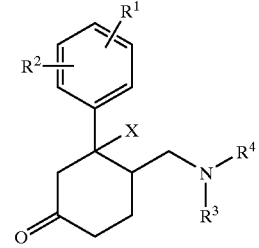

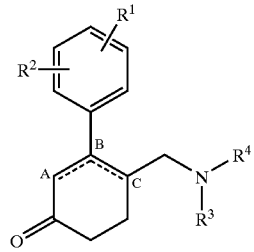

wherein $R^1$ and $R^2$ independently of one another are $R^5$ or $YR^5$, wherein Y is $C_1$–$C_{10}$-alkyl, $C_2$–$C_{10}$-alkenyl or $C_2$–$C_{10}$ alkinyl, branched or unbranched and mono- or polysubstituted or unsubstituted, wherein $R^5$ is H; F; Cl; Br; I; CN; $NO_2$; $C_1$–$C_8$-alkyl, $C_2$–$C_8$-alkenyl or $C_2$–$C_8$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by an S, O or $NR^6$, wherein $R^6$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;

aryl or heteroaryl, in each case mono- or polysubstituted or unsubstituted;

$OR^7$, $OC(O)R^7$, $OC(O)OR^7$, $OC(S)R^7$, $C(O)R^7$, $C(O)OR^7$, $C(S)R^7$, $C(S)OR^7$, $SR^7$, $S(O)R^7$ or $S(O_2)R^7$, wherein $R^7$ is H; $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by an S, O or $NR^8$, where $R^8$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted; or alkylaryl, saturated or unsaturated and mono- or polysubstituted or unsubstituted; or aryl or heteroaryl, in each case mono- or polysubstituted or unsubstituted; or $NR^9R^{10}$, $C(O)NR^9R^{10}$ or $S(O_2)NR^9R^{10}$, wherein $R^9$ and $R^{10}$ independently of one another are H; $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by S, O or $NR^{11}$, wherein $R^{11}$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted; or alkylaryl, saturated or unsaturated and mono- or polysubstituted or unsubstituted; aryl or heteroaryl, in each case mono- or polysubstituted or unsubstituted; or $R^9$ and $R^{10}$ together form a $C_3$–$C_7$-cycloalkyl, saturated or unsaturated and mono- or polysubstituted or unsubstituted, or a corresponding heterocyclic radical, in which one carbon atom in the ring is replaced by an S, O or $NR^{12}$, where $R^{12}$ is chosen from H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted; or $R^1$ and $R^2$ together form —CH=CH—CH=CH—, resulting in a naphthyl system which can be mono- or polysubstituted, X is H; F; Cl; Br; I; $CF_3$; O—$S(O_2)$—$C_6H_4$-$pCH_3$; $OR^{13}$ or $OC(O)R^{13}$, wherein $R^{13}$ is H; $C_1$–$C_{10}$-alkyl, $C_2$–$C_{10}$-alkenyl or $C_2$–$C_{10}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by an N, S or O; alkylaryl, saturated or unsaturated and mono- or polysubstituted or unsubstituted; or aryl or heteroaryl, in each case mono- or polysubstituted or unsubstituted; or if according to formula Ia the compound contains no X, a double bond is formed between carbon atoms "A" and "B", or carbon atoms "B" and "C"; and $R^3$, $R^4$ independently of one another are H; $C_1$–$C_{10}$-alkyl, $C_2$–$C_{10}$-alkenyl or $C_2$–$C_{10}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one carbon atom in the ring is replaced by an N, S or O; alkylaryl, saturated or unsaturated and mono- or polysubstituted or unsubstituted; or aryl or heteroaryl, in each case mono- or polysubstituted or unsubstituted; or $R^3$ and $R^4$ together form a $C_3$–$C_7$-cycloalkyl, saturated or unsaturated and mono- or polysubstituted or unsubstituted, or a corresponding heterocyclic radical, in which one carbon atom in the ring is replaced by an S, O or $NR^{14}$, wherein $R^{14}$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted, or a diastereomer, enantiomer thereof, or a salt formed with a physiologically tolerated acid, and a pharmaceutically acceptable excipient.

71. A pharmaceutical composition according to claim 70, wherein the salt formed with a physiologically tolerated acid is a hydrochloride salt.

72. A pharmaceutical composition according to claim 70, wherein $R^1=R^5$, and $R^5$ is H; F; Cl; Br; I; $CHF_2$; $CF_3$; $NO_2$; $NH_2$; $C_1$–$C_4$-alkyl or $C_2$–$C_4$-alkenyl, branched or unbranched and mono- or polysubstituted or unsubstituted; aryl, substituted or unsubstituted; $OR^7$, $C(O)OR^7$ or $SR^7$, wherein $R^7$ is H or branched or unbranched and mono- or polysubstituted or unsubstituted $C_1$–$C_4$-alkyl; or $S(O_2)NR^9R^{10}$, wherein $R^9$ and $R^{10}$ independently of one another are H or branched or unbranched and mono- or polysubstituted or unsubstituted $C_1$–$C_4$-alkyl.

73. A pharmaceutical according to claim 72, wherein $R^1=R^5$, and $R^7$ is H, $CF_3$ or $CH_3$.

74. A pharmaceutical according to claim 72, wherein $R^5$ is selected from the group consisting of H, F, Cl, OH, $CH_3$, $C_2H_5$, $C_2H_3$, $CHF_2$, $CF_3$, $SCH_3$, $OCF_3$, $OCH_3$, $OC_2H_5$, $C(O)OCH_3$, $C(O)OC_2H_5$ and phenyl.

75. A pharmaceutical composition according to claim 70, wherein $R^2=R^5$, and $R^5$ is H; F; Cl; Br; I; $SCH_3$; $C_1$–$C_4$-alkyl, $C_2$–$C_4$-alkenyl, branched or unbranched and mono- or polysubstituted or unsubstituted, preferably $CF_3$; or $OR^7$, where $R^7$ is branched or unbranched and mono- or polysubstituted or unsubstituted $C_1$–$C_4$-alkyl.

76. A pharmaceutical composition according to claim 75, wherein $R^2=R^5$, and $R^7$ is $CH_3$.

77. A pharmaceutical composition according to claim 70, wherein $R^1$ and $R^2$ have different meanings, or $R^1$ and $R^2$ together form —CH=CH—CH=CH—, resulting in a naphthyl system which is unsubstituted, monosubstituted or polysubstituted.

78. A pharmaceutical composition according to claim 77, wherein the naphthyl system is mono- or polysubsituted by halogen, $OC_{1-3}$-alkyl or $C_{1-3}$-alkyl.

79. A pharmaceutical composition according to claim 77, wherein the naphthyl system is mono- or polysubsituted by $OCH_3$.

80. A pharmaceutical composition according to claim 70, wherein X is

H; F; Cl; OH; $CF_3$; O—$S(O_2)$—$C_6H_4$-$pCH_3$; or $OC(O)R^7$, wherein $R^7$ is H, or $C_1$–$C_4$-alkyl or $C_2$–$C_4$-alkenyl, branched or unbranched and mono- or polysubstituted or unsubstituted, or if according to formula Ia the compound contains no X, a double bond is formed between carbon atoms "A" and "B", or carbon atoms "B and "C".

81. A pharmaceutical composition according to claim 79, wherein X is H; F; Cl; OH; O—$S(O_2)$—$C_6H_4$-$pCH_3$; or $OC(O)R^7$, where $R^7=C_1$–$C_4$-alkyl.

82. A pharmaceutical composition of claim 80, wherein X is $O(C)OCH_3$.

83. A pharmaceutical composition of claim 80, wherein X is H or OH.

84. A pharmaceutical composition according to claim 70, wherein $R^3$ and $R^4$ independently of one another are branched or unbranched and mono- or polysubstituted or unsubstituted $C_1$–$C_4$-alkyl; or $R^3$ and $R^4$ together form a saturated or unsaturated and mono- or polysubstituted or unsubstituted $C_3$–$C_7$-cycloalkyl.

85. A pharmaceutical composition according to claim 83, wherein $R^3$ and $R^4$ independently of one another are $CH_3$.

86. A pharmaceutical composition according to claim 70, wherein $R^1=R^5$, and $R^5$ is H; F; Cl; Br; I; $CHF_2$; $CF_3$; $NO_2$; $NH_2$; $C_1$–$C_4$-alkyl or $C_2$–$C_4$-alkenyl, branched or unbranched and mono- or polysubstituted or unsubstituted; aryl, substituted or unsubstituted; $OR^7$, $C(O)OR^7$ or $SR^7$, wherein $R^7$ is H or branched or unbranched and mono- or polysubstituted or unsubstituted $C_1$–$C_4$-alkyl; or $S(O_2)NR^9R^{10}$, wherein $R^9$ and $R^{10}$ independently of one another are H or branched or unbranched and mono- or polysubstituted or unsubstituted $C_1$–$C_4$-alkyl, and $R^2=R^5$, and $R^5$ is H; F; Cl; Br; I; $SCH_3$; $C_1$–$C_4$-alkyl, $C_2$–$C_4$-alkenyl, branched or unbranched and mono- or polysubstituted or unsubstituted, preferably $CF_3$; or $OR^7$, where $R^7$ is branched or unbranched and mono- or polysubstituted or unsubstituted $C_1$–$C_4$-alkyl, or $R^1$ and $R^2$ together form —CH=CH—CH=CH—, resulting in a naphthyl system which is unsubstituted, monosubstituted or polysubstituted, and X is H; F; Cl; OH; $CF_3$; O—$S(O_2)$—$C_6H_4$-$pCH_3$; or $OC(O)R^7$, wherein $R^7$ is H, or $C_1$–$C_4$-alkyl or $C_2$–$C_4$-alkenyl, branched or unbranched and mono- or polysubstituted or unsubstituted, or if according to formula Ia the compound contains no X, a double bond is formed between carbon atoms "A" and "B", or carbon atoms "B and C", and $R^3$ and $R^4$ independently of one another are branched or unbranched and mono- or polysubstituted or unsubstituted $C_1$–$C_4$-alkyl; or $R^3$ and $R^4$ together form a saturated or unsaturated and mono- or polysubstituted or unsubstituted $C_3$–$C_7$-cycloalkyl.

87. A pharmaceutical composition according to claim 70, wherein the aminomethyl-phenyl-cyclohexanone derivative is selected from the group consisting of rac-cis-[4-dimethylaminomethyl-3-hydroxy-3-(3-methoxy-phenyl)-cyclohexanone];

rac-cis-[4-dimethylaminomethyl-3-(3-methoxy-phenyl)-cyclohexanone];

rac-trans-[4-dimethylaminomethyl-3-(3-methoxy-phenyl)-cyclohexanone];

rac-cis-[4-dimethylaminomethyl-3-(3-hydroxy-phenyl)-cyclohexanone];

rac-trans-[4-dimethylaminomethyl-3-(3-hydroxy-phenyl)-cyclohexanone];

4-dimethylaminomethyl-3-(3-methoxy-phenyl)-cyclohex-2-enone;

4-dimethylaminomethyl-3-phenyl-cyclohex-2-enone;

4-dimethylaminomethyl-3-(3-hydroxy-phenyl)-cyclohex-2-enone;

rac-trans-4-dimethylaminomethyl-3-phenyl-cyclohexanone;

rac-cis-4-dimethylaminomethyl-3-phenyl-cyclohexanone;

4-dimethylaminomethyl-3-(4-methoxy-phenyl)-cyclohex-2-enone;

4-dimethylaminomethyl-3-naphthalen-2-yl-cyclohex-2-enone;

rac-trans-4-dimethylaminomethyl-3-hydroxy-3-naphthalen-2-yl-cyclohexanone;

rac-trans-4-dimethylaminomethyl-3-(3-fluoro-phenyl)-cyclohexanone;

rac-cis-4-dimethylaminomethyl-3-(3-fluoro-phenyl)-cyclohexanone;

rac-cis-4-dimethylaminomethyl-3-hydroxy-3-(2-methoxy-phenyl)-cyclohexanone rac-cis-4-dimethylaminomethyl-3-hydroxy-3-(6-methoxy-naphthalen-2-yl)-cyclohexanone;

4-dimethylaminomethyl-3-(6-methoxy-naphthalen-2-yl)-cyclohex-2-enone;

rac-cis-3-biphenyl-4-yl-4-dimethylaminomethyl-3-hydroxy-cyclohexanone 3-(3-difluoromethyl-phenyl)-4-dimethylaminomethyl-cyclohex-2-enone;

4-dimethylaminomethyl-3-(3-fluoro-phenyl)-cyclohex-2-enone;

3-(3,4-difluoro-phenyl)-4-dimethylaminomethyl-cyclohex-2-enone;

4-dimethylaminomethyl-3-(4-fluoro-phenyl)-cyclohex-2-enone;

4-dimethylaminomethyl-3-(4-trifluoromethyl-phenyl)-cyclohex-2-enone;

3-(3,5-dichloro-phenyl)-4-dimethylaminomethyl-cyclohex-2-enone;

3-(3,5-difluoro-phenyl)-4-dimethylaminomethyl-cyclohex-2-enone; and rac-cis-3-(3,5-difluoro-phenyl)-4-dimethylaminomethyl-3-hydroxy-cyclohexanone.

88. A method for treating pain, comprising administering an effective pain-treating amount of a pharmaceutical composition of claim 70 to a patient in need thereof.

89. A method for treating at least one condition selected from the group consisting of inflammatory reaction, allergic reactions, depression, drug abuse, alcohol abuse, gastritis, cardiovascular disease, respiratory tract disease, coughing, mental illness, epilepsy, urinary incontinence, itching, and diarrhoea, comprising administering an effective pain-treating amount of a pharmaceutical composition of claim 70 to a patient in need thereof.

* * * * *